(12) United States Patent
Zhou et al.

(10) Patent No.: US 9,328,125 B2
(45) Date of Patent: May 3, 2016

(54) BIVALENT AMPA RECEPTOR POSITIVE ALLOSTERIC MODULATORS

(71) Applicants: Jia Zhou, League City, TX (US); Haijun Chen, Galveston, TX (US); Kenneth M Johnson, Galveston, TX (US); Cheng Z Wang, Galveston, TX (US)

(72) Inventors: Jia Zhou, League City, TX (US); Haijun Chen, Galveston, TX (US); Kenneth M Johnson, Galveston, TX (US); Cheng Z Wang, Galveston, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 14/474,258

(22) Filed: Sep. 1, 2014

(65) Prior Publication Data

US 2015/0057248 A1   Feb. 26, 2015

Related U.S. Application Data

(63) Continuation-in-part of application No. PCT/US2013/027878, filed on Feb. 27, 2013.

(60) Provisional application No. 61/605,631, filed on Mar. 1, 2012.

(51) Int. Cl.
| | |
|---|---|
| *C07D 471/04* | (2006.01) |
| *C07D 213/82* | (2006.01) |
| *C07D 209/08* | (2006.01) |
| *C07D 209/14* | (2006.01) |
| *C07D 401/06* | (2006.01) |
| *C07C 311/03* | (2006.01) |
| *C07F 5/02* | (2006.01) |
| *C07D 231/56* | (2006.01) |
| *C07D 401/12* | (2006.01) |
| *C07D 207/27* | (2006.01) |

(52) U.S. Cl.
CPC ............... *C07F 5/025* (2013.01); *C07C 311/03* (2013.01); *C07D 207/27* (2013.01); *C07D 209/08* (2013.01); *C07D 209/14* (2013.01); *C07D 213/82* (2013.01); *C07D 231/56* (2013.01); *C07D 401/06* (2013.01); *C07D 401/12* (2013.01); *C07D 471/04* (2013.01)

(58) Field of Classification Search
None
See application file for complete search history.

(56) References Cited

U.S. PATENT DOCUMENTS

| | | | | |
|---|---|---|---|---|
| 6,303,816 B1 * | 10/2001 | Arnold et al. | .................... | 564/82 |
| 6,790,844 B2 * | 9/2004 | Ueno et al. | .................... | 514/183 |
| 2003/0225127 A1 * | 12/2003 | Bender et al. | ................. | 514/312 |

* cited by examiner

*Primary Examiner* — Timothy R Rozof
(74) *Attorney, Agent, or Firm* — Norton Rose Fulbright US LLP

(57) ABSTRACT

Embodiments of the invention are directed to compounds that are positive allosteric modulators of AMPA receptors.

8 Claims, 9 Drawing Sheets

BIVALENT AMPA RECEPTOR POSITIVE ALLOSTERIC MODULATORS

PRIORITY CLAIM

This application is a continuation-in-part of International application serial number PCT/US2013/027878 filed Feb. 27, 2013, which claims priority to U.S. Provisional Patent Application Ser. No. 61/605,631 filed Mar. 1, 2012. Priority is claimed to both applications referenced above, each of which is incorporated herein by reference in its entirety.

STATEMENT REGARDING FEDERALLY FUNDED RESEARCH

This invention was made with government support under P30 (DA028821) awarded by the NIDA/NIH. The government has certain rights in the invention.

BACKGROUND

α-Amino-3-hydroxy-5-methyl-4-isoxazolepropionic acid receptors (AMPARs) are a major class of ionotropic glutamate receptors that mediate the majority of fast excitatory synaptic transmission in the mammalian brain (Ozawa et al., *Prog Neurobiol.* 54(5): 581-618, 1998). The interdependency between AMPARs and N-methy-D-aspartate receptors (NMDARs) makes AMPARs a promising target for therapeutic intervention of NMDAR-mediated glutamatergic hypofunction. AMPAR activation is essential for NMDAR neurotransmission since the activation of AMPARs induces the depolarization of postsynaptic membranes, which relieves the $Mg^{2+}$ block of the NMDAR channels (Lynch, *Nat Neurosci* 5 Suppl:1035-1038, 2002), and in turn enhances synaptic efficacy and augments glutamatergic neurotransmission (Arai et al., *Neuroscience* 123(4): 1011-1024, 2004). Moreover, NMDAR activation is essential for the recruitment of AMPA receptors to the membrane at activated synaptic sites (Sun et al., *J Neurosci* 25(32): 7342-7351, 2005). Direct activation of glutamate receptors by agonists to correct glutamatergic hypofunction increases the risk of excitotoxicity and additional neuronal damage. AMPAR positive allosteric modulators (PAMs) do not activate the receptor directly, but have been shown to increase receptor affinity for agonist (Arai et al., *Neuroreport.* 7(13):2211-5, 1996), reduce receptor desensitization and deactivation (Granger et al., *Synapse* 15(4): 326-329, 1993; Arai et al, *Mol Pharmacol* 58(4):802-13, 2000; Lynch and Gall, *Trends Neurosci* 29(10): 554-562, 2006), and enhance the induction of LTP both in vitro (Arai et al, *Neuroreport.* 7(13):2211-5, 1996) and in vivo (Staubli et al., *PNAS* 91 (23):11158-62, 1994). AMPAR PAMs also improve performance in a radial arm maze task assessing spatial working memory (O'Neill et al., *Curr Drug Targets CNS Neurol Disord* 3(3): 181-194, 2004; Quirk and Nisenbaum, *CNS Drug Rev* 8(3): 255-282, 2002), and robustly ameliorate ketamine-induced impairment of working memory (Roberts et al., *Behav Brain Res* 212(1): 41-48, 2010). Thus, discovery of new AMPAR PAMs aimed at correcting NMDAR-mediated glutamatergic hypofunction is needed to moderate or prevent situations associated with diminished NMDAR function. Therefore, bivalent AMPAR PAMs can be used as therapeutics for cognitive abnormalities involving glutamatergic hypofunction including schizophrenia, Alzheimer's disease, Parkinson's disease, addiction, and attention deficit hyperactivity disorder (ADHD).

AMPARs consist of a family of tetrameric receptors arising from four genes, each of which encodes a distinct receptor subunit (GluA1-4), each of which can undergo alternative splicing of a 38 amino acid sequence in the extracellular region just before the fourth membrane spanning domain M4 resulting in so called "flip" and "flop" splice variants (Ward et al., *Br J Pharmacol* 160(2): 181-190, 2010). It was recently revealed that the binding site for allosteric activators at the dimer interface actually consists of a large surface with several subsites (Ahmed et al., *J Med Chem* 53(5):2197-2203, 2010). This rather large surface with non-overlapping subsites suggests a means by which agonist affinity can be increased, that is, by generating bivalent or even multivalent compounds that can interact with different subsites.

SUMMARY

Recent studies on binding modes strongly support the design of new bivalent or even multivalent AMPAR PAMs. The inventors have been investigating asymmetric bivalent ligands that target the two binding domains, especially the AMPAR heterodimeric subunits such as GluA1 flip ($GluA1_i$) and/or GluA3 flip ($GluA3_i$) to design highly potent and specific AMPAR PAMs. The overall design approach was governed by classic guidelines such as Log P and tPSA calculations, molecular weight and volume, and Lipinski's Rule of Five, as well as the preliminary data. As depicted in FIG. 5, two asymmetric binding sites (S1 and S2) are introduced into the indole, azaindole, indazole, pyridine, or benzothiazole scaffolds based upon lead molecules to systematically investigate bivalent ligands to improve the potency and specificity as well as drug-likeness (e.g. solubility and blood-brain barrier penetration capability). The binding domains include the arylpropylsulfonamide moiety, and an amide (compounds A1-4 and A5-9), a sulfonamide (compounds B1-9 and C1-2), or a phenylsulfone (compounds C3-4; to compare with the sulfonamide analogs), or a lactam (compounds D1-5) moiety as the second binding domain. The reason for choosing the indole, azaindole, indazole, pyridine, or benzothiazole as the parent scaffolds is that they are important pharmacophores for the bioisosteric replacement of the aryl or heteroaryl components in either existing AMPAR allosteric modulators such as the CX series or other new chemotypes such as the pyrrole (Zarrinmayeh et al, *Bioorg Med Chem Lett* 16(19): 5203-6, 2006) and 4,5,6,7-tetrahydro-1H-indazole (Bradley et al, PCT publ. WO2007/107539) analogs initially identified with the advent of high-throughput screening technologies. Moreover, the indole, azaindole, pyridine, or indazole scaffold itself offers an ideal platform with multiple positions, including the 1, 3, 5, and 6-positions, which are suitable for the chemical introduction of two binding domains.

Certain embodiments are directed to specific bivalent positive allosteric modulators (PAMs) of AMPA receptor (AMPAR) that will enhance glutamatergic neurotransmission, and in turn, prevent the effects of phencyclidine (PCP), a selective NMDA open channel blocker on developmental neuroapoptosis. The newly identified AMPAR PAMs will help compensate for diminished excitatory neurotransmission in the treatment of human cognitive deficit diseases, including schizophrenia and Alzheimer's.

Certain embodiments are directed to a positive allosteric modulator of AMPA receptors having a general formula of Formula I:

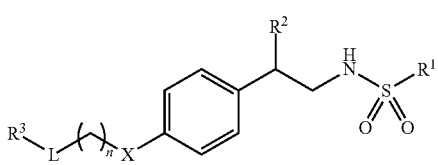

Formula I where $R^1$ and $R^2$ are independently hydrogen, $C_1$-$C_6$ alkyl or $C_1$-$C_6$ heteroalkyl; X is aryl or heteroaryl; n is 0, 1, 2, 3, 4, 5, or 6; L is a direct bond, —NH—, —C(O)—, or —C(O)NH—; and $R^3$ is hydrogen, nitro, amine, cyano, substituted or unsubstituted sulfonyl, substituted or unsubstituted acyl, substituted or unsubstituted alkyl, substituted or unsubstituted heteroalkyl, substituted or unsubstituted cycloalkyl, substituted or unsubstituted heterocyclyl, substituted or unsubstituted aryl, or a substituted or unsubstituted heteroaryl. The linker L can be incorporated in either direction (e.g., —C(O)NH— or —NHC(O)—). In certain aspects X is a monocyclic or polycyclic heteroaryl when n is 0, 1, 2, 3, 4, 5, or 6, or an aryl when n is 1, 2, 3, 4, 5, or 6. In a further aspects L is a —NH—, —C(O)—, or —C(O)NH—.

In some embodiment, $R^3$ is substituted by $R^4$, where $R^4$ is oxo, nitro, amine, cyano, substituted or unsubstituted sulfonyl, substituted or unsubstituted acyl, substituted or unsubstituted alkyl, substituted or unsubstituted heteroalkyl, substituted or unsubstituted cycloalkyl, substituted or unsubstituted heterocyclyl, substituted or unsubstituted aryl, or a substituted or unsubstituted heteroaryl.

In certain aspects, X is a phenyl, indole, azaindole, indazole, pyridine, or benzothiazole.

Certain embodiments are directed to a compound of Formula I where X is an indole; and $R^1$ and $R^2$ are as described above, n is 0, L is a direct bond, and $R^3$ is hydrogen, nitro, amine, cyano, or substituted or unsubstituted sulfonyl.

Certain embodiments are directed to a compound of Formula I where X is an indole or azaindole; and $R^1$ and $R^2$ are as described above; n is 0, L is —C(O)—; and $R^3$ is substituted or unsubstituted nitrogen containing $C_5$-$C_6$ heterocycle, or substituted or unsubstituted nitrogen containing $C_5$-$C_6$ heteroaryl. In certain aspects the azaindole is a 4-, 5-, 6-, or 7-azaindole. In certain aspects the nitrogen containing heterocycle is substituted or unsubstituted pyrrolidine, substituted or unsubstituted piperidine, substituted or unsubstituted piperazine. In a further aspect, the substituted pyrrolidine is 2-, 3-, 4-, 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is an indole or azaindole; and $R^1$ and $R^2$ are as described above; n is 0, 1, 2, or 3; L is —C(O)NH—, and $R^3$ is substituted or unsubstituted nitrogen containing $C_5$-$C_6$ heterocycle, or substituted or unsubstituted nitrogen containing $C_5$-$C_6$ heteroaryl. In certain aspects, azaindole is a 4-, 5-, 6-, or 7-azaindole. In certain aspects the nitrogen containing heterocycle is substituted or unsubstituted pyrrolidine, substituted or unsubstituted piperidine, substituted or unsubstituted piperazine. In a further aspect, the substituted pyrrolidine is 2-, 3-, 4-, 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is an indazole; and $R^1$ and $R^2$ are as described above; n is 0, 1, 2, or 3; L is a direct bond; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is an indazole; and $R^1$ and $R^2$ are as described above; n is 0, 1, 2, or 3; L is N; and $R^3$ is substituted or unsubstituted sulfonyl, nitrogen containing $C_5$-$C_6$ heterocycle or a nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is an indazole; and $R^1$ and $R^2$ are as described above, n is 0, L is —C(O)—, and $R^3$ is nitrogen containing $C_5$-$C_6$ heterocycle or a nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is an indazole; and $R^1$ and $R^2$ are as described above; n is 0, 1, 2, or 3; L is —C(O)NH—; and $R^3$ is substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the substituted or unsubstituted aryl is a substituted or unsubstituted phenyl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is pyrimidine; and $R^1$ and $R^2$ are as described above; n is 0, 1, 2, or 3; L is a direct bond; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is pyrimidine; and $R^1$ and $R^2$ are as described above; n is 0; L is —C(O)—; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is pyrimidine; and $R^1$ and $R^2$ are as described above; n is 0, 1, 2, or 3; L is —C(O)NH—; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is benzothiazole; and $R^1$ and $R^2$ are as described above; n is 0, 1, 2, or 3; L is a direct bond; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4 pyridyl. In certain aspects the nitrogen containing heterocycle is substituted with hydroxyl, methyl, sulfonyl, or acetyl.

Certain embodiments are directed to a compound of Formula I where X is benzothiazole; and $R^1$ and $R^2$ are as described above; n is 0; L is —C(O)—; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4-pyridyl. In certain aspects the nitrogen containing heterocycle is substituted with hydroxyl, methyl, sulfonyl, or acetyl.

Certain embodiments are directed to a compound of Formula I where X is benzothiazole; and $R^1$ and $R^2$ are as described above; n is 0, 1, 2, or 3; L is —C(O)NH—; and $R^3$ is substituted or unsubstituted sulfonyl, substituted or unsubstituted aryl, substituted or unsubstituted heteroaryl, substituted or unsubstituted nitrogen containing $C_5$-$C_6$ heterocycle or substituted or unsubstituted nitrogen containing $C_5$-$C_6$ heteroaryl. In certain aspects the nitrogen containing heterocycle is substituted or unsubstituted pyrrolidine, substituted or unsubstituted piperidine, substituted or unsubstituted piperazine. In certain aspects the substituted pyrrolidine is 2-, 3-, 4-, or 5-oxo-pyrrolidine. In a further aspect the substituted or unsubstituted nitrogen containing heteroaryl is 2-pyridyl, 3-pyridyl, or 4-pyridyl. In certain aspects the nitrogen containing heterocycle is substituted with hydroxyl, methyl, sulfonyl, or acetyl.

Certain embodiments are directed to a positive allosteric modulator of AMPA receptors having a general formula of Formula II:

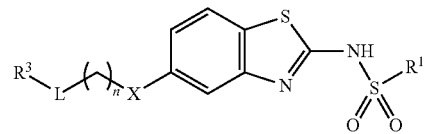

Formula II where $R^1$, $R^3$, X, n, and L are as described above for Formula I.

Certain embodiments are directed to one or more positive allosteric modulator of AMPA receptors selected from Propane-2-sulfonic acid (2-{4-[2-(pyrrolidine-1-carbonyl)-pyridin-4-yl]-phenyl}-propyl)-amide (HJC-1-22); Propane-2-sulfonic acid (2-{4-[5-(piperidine-1-carbonyl)-indol-1-yl]-phenyl}-propyl)amide (HJC-1-24); Propane-2-sulfonic acid (2-{4-[5-(piperidine-1-carbonyl)-pyridin-2-yl]-phenyl}-propyl)-amide (HJC-1-59); Propane-2-sulfonic acid (2-{4'-[2-(2-oxo-pyrrolidin-1-yl)-ethyl]-biphenyl-4-yl}-propyl)amide (HJC-1-73); Propane-2-sulfonic acid {2-[4-(5-nitro-indol-1-yl)-phenyl]-propyl}amide (HJC-1-79); Propane-2-sulfonic acid {2-[4-(5-amino-indol-1-yl)-phenyl]-propyl}amide (HJC-1-86); Propane-2-sulfonic acid (2-{4-[5-(piperidine-1-carbonyl)-indazol-1-yl]-phenyl}-propyl)-amide (HJC-2-8); Propane-2-sulfonic acid (2-{4-[5-(pyrrolidine-1-carbonyl)-indol-1-yl]-phenyl}-propyl)amide (HJC-2-10); Propane-2-sulfonic acid (2-{4-[5-(4-methyl-piperazine-1-carbonyl)-indol-1-yl]-phenyl}-propyl)amide (HJC-2-22); Propane-2-sulfonic acid [2-(4-pyrrolo[2,3-b]pyridin-1-yl-phenyl)-propyl]amide (HJC-2-28); Propane-2-sulfonic acid [2-(4-pyrrolo[3,2-b]pyridin-1-yl-phenyl)-propyl]amide (HJC-2-29); Propane-2-sulfonic acid [2-(4-pyrrolo[3,2-c]pyridin-1-yl-phenyl)-propyl]amide (HJC-2-31); Propane-2-sulfonic acid [2-(4-pyrrolo[2,3-c]pyridin-1-yl-phenyl)-propyl]amide (HJC-2-32); Propane-2-sulfonic acid (2-{4-[5-(piperazine-1-carbonyl)-indol-1-yl]-phenyl}-propyl)amide (HJC-2-37); Propane-2-sulfonic acid {2-[4-(5-cyano-indol-1-yl)-phenyl]-propyl}amide (HJC-2-35); Propane-2-sulfonic acid [2-(4-indol-1-yl-phenyl)-propyl]amide (HJC-2-46); Pyridine-2-carboxylic acid (1-{4-[1-methyl-2-

(propane-2-sulfonylamino)-ethyl]-phenyl}-1H-indol-5-yl)amide (HJC-2-48); Propane-2-sulfonic acid (2-{4-[5-(4-methanesulfonyl-piperazine-1-carbonyl)-indol-1-yl]-phenyl}-propyl)amide (HJC-2-67); Propane-2-sulfonic acid (2-{4-[5-(4-acetyl-piperazine-1-carbonyl)-indol-1-yl]-phenyl}-propyl)amide (HJC-2-68); Propane-2-sulfonic acid (2-{4-[2-(piperidine-1-carbonyl)-pyridin-4-yl]-phenyl}-propyl)-amide (HJC-2-69); or Propane-2-sulfonic acid (2-{4-[5-(pyrrolidine-1-carbonyl)-pyridin-2-yl]-phenyl}-propyl)-amide (HJC-2-70).

TABLE 1

List of representative compounds.

| Compound code | Structure |
|---|---|
| HJC-1-22 | 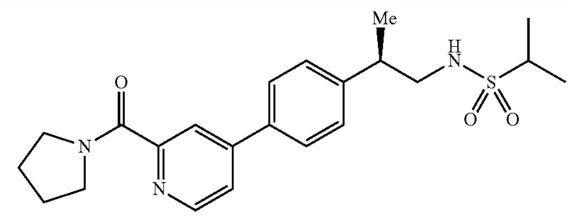 [SMILES: CC(C)S(=O)(=O)NC[C@H](C)c1ccc(-c2ccnc(C(=O)N3CCCC3)c2)cc1] |
| HJC-1-24 | 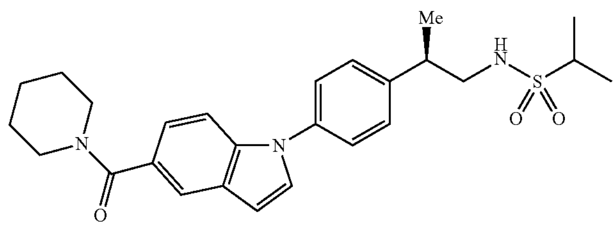 [SMILES: CC(C)S(=O)(=O)NC[C@H](C)c1ccc(-n2ccc3cc(C(=O)N4CCCCC4)ccc32)cc1] |
| HJC-1-59 | 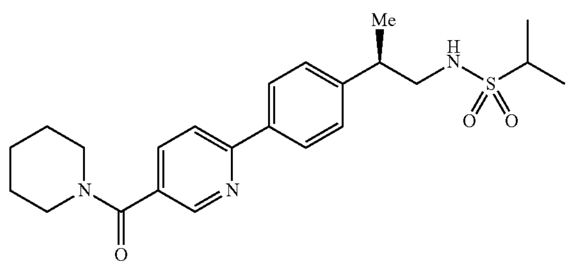 [SMILES: CC(C)S(=O)(=O)NC[C@H](C)c1ccc(-c2ccc(C(=O)N3CCCCC3)cn2)cc1] |
| HJC-1-73 | 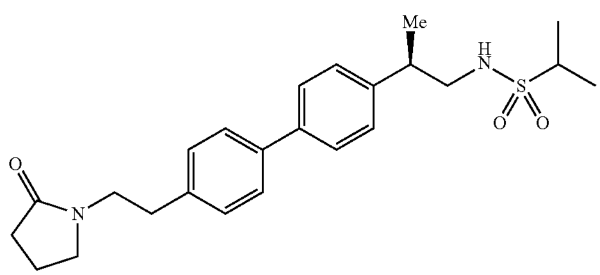 [SMILES: CC(C)S(=O)(=O)NC[C@H](C)c1ccc(-c2ccc(CCN3CCCC3=O)cc2)cc1] |
| HJC-1-79 | 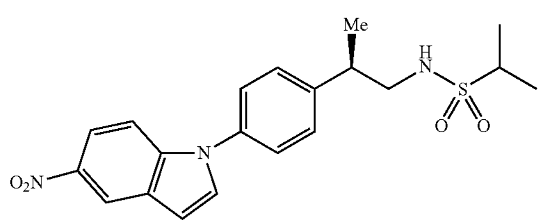 |
| HJC-1-86 | 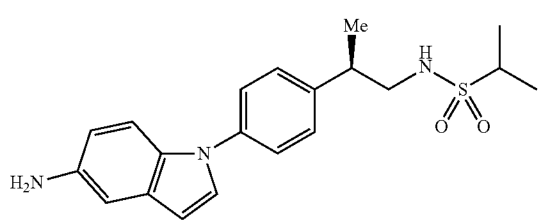 [SMILES: CC(C)S(=O)(=O)NC[C@H](C)c1ccc(-n2ccc3cc(N)ccc32)cc1] |

TABLE 1-continued

List of representative compounds.

| Compound code | Structure |
| --- | --- |
| HJC-2-8 | 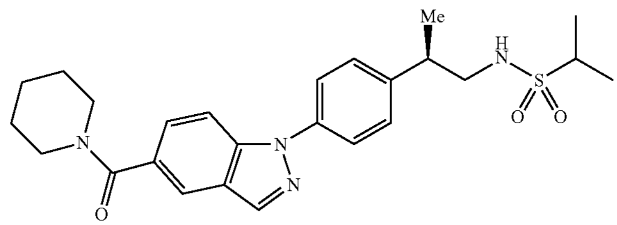 [SMILES: CC(C)S(=O)(=O)NC[C@H](C)c1ccc(-n2ncc3cc(C(=O)N4CCCCC4)ccc32)cc1] |
| HJC-2-10 | 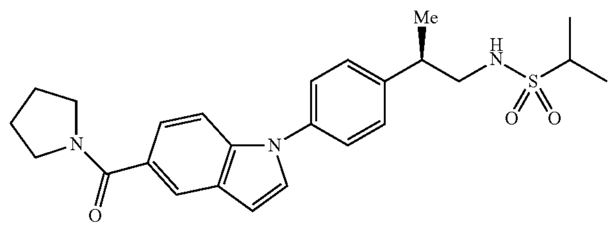 [SMILES: CC(C)S(=O)(=O)NC[C@H](C)c1ccc(-n2ccc3cc(C(=O)N4CCCC4)ccc32)cc1] |
| HJC-2-22 | 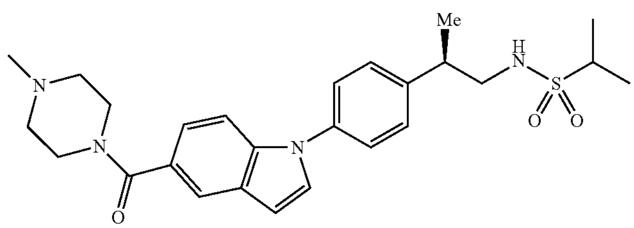 [SMILES: CC(C)S(=O)(=O)NC[C@H](C)c1ccc(-n2ccc3cc(C(=O)N4CCN(C)CC4)ccc32)cc1] |
| HJC-2-28 | 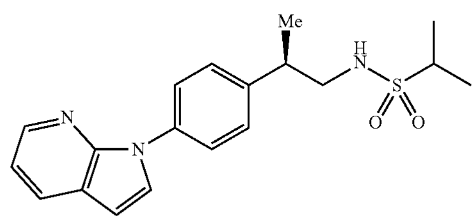 [SMILES: CC(C)S(=O)(=O)NC[C@H](C)c1ccc(-n2ccc3cccnc32)cc1] |
| HJC-2-29 | 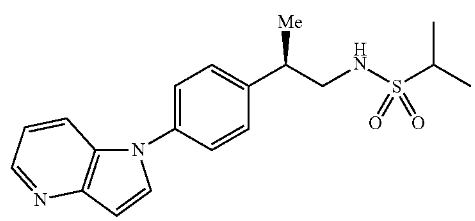 [SMILES: CC(C)S(=O)(=O)NC[C@H](C)c1ccc(-n2ccc3ncccc32)cc1] |
| HJC-2-31 | 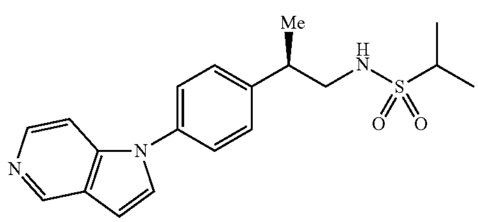 [SMILES: CC(C)S(=O)(=O)NC[C@H](C)c1ccc(-n2ccc3cnccc32)cc1] |
| HJC-2-32 | 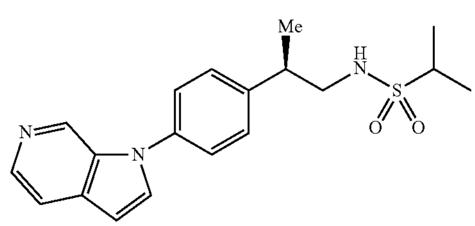 [SMILES: CC(C)S(=O)(=O)NC[C@H](C)c1ccc(-n2ccc3ccncc32)cc1] |

TABLE 1-continued

List of representative compounds.

| Compound code | Structure |
|---|---|
| HJC-2-35 | 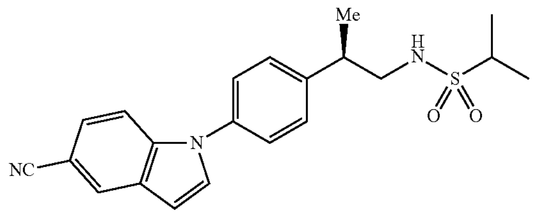 [SMILES: CC(C)S(=O)(=O)NC[C@H](C)c1ccc(-n2ccc3cc(C#N)ccc32)cc1] |
| HJC-2-37 | 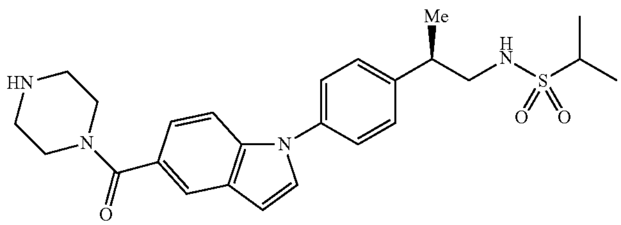 [SMILES: CC(C)S(=O)(=O)NC[C@H](C)c1ccc(-n2ccc3cc(C(=O)N4CCNCC4)ccc32)cc1] |
| HJC-2-46 | 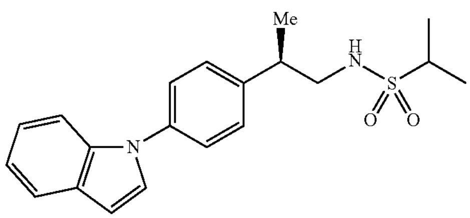 [SMILES: CC(C)S(=O)(=O)NC[C@H](C)c1ccc(-n2ccc3ccccc32)cc1] |
| HJC-2-48 | 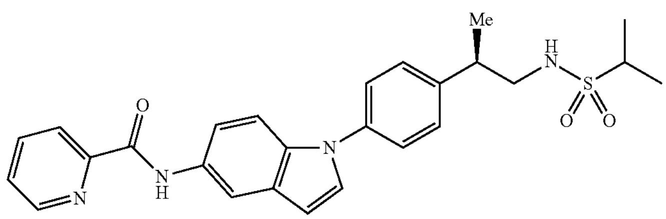 [SMILES: CC(C)S(=O)(=O)NC[C@H](C)c1ccc(-n2ccc3cc(NC(=O)c4ccccn4)ccc32)cc1] |
| HJC-2-67 | 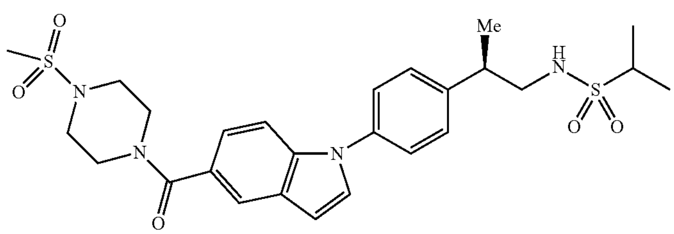 [SMILES: CC(C)S(=O)(=O)NC[C@H](C)c1ccc(-n2ccc3cc(C(=O)N4CCN(S(C)(=O)=O)CC4)ccc32)cc1] |
| HJC-2-68 | 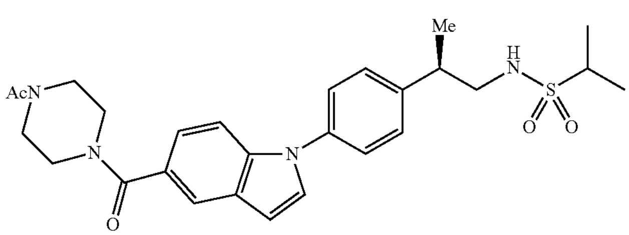 |
| HJC-2-69 | 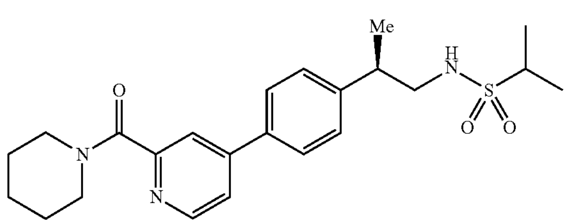 [SMILES: CC(C)S(=O)(=O)NC[C@H](C)c1ccc(-c2ccnc(C(=O)N3CCCCC3)c2)cc1] |

TABLE 1-continued

List of representative compounds.

| Compound code | Structure |
|---|---|
| HJC-2-70 | *(chemical structure: 4-methylpiperazinyl... pyridine with pyrrolidine carbonyl, phenyl, and N-isopropylsulfonamide side chain with Me stereocenter)* |

Certain embodiments are directed to methods for providing neuroprotection comprising administering a neuroprotective compound described herein. In certain aspects the neuroprotective compound is selected from Propane-2-sulfonic acid (2-{4-[2-(pyrrolidine-1-carbonyl)-pyridin-4-yl]-phenyl}-propyl)-amide (HJC-1-22); Propane-2-sulfonic acid (2-{4-[5-(piperidine-1-carbonyl)-indol-1-yl]-phenyl}-propyl)amide (HJC-1-24); Propane-2-sulfonic acid (2-{4-[5-(piperidine-1-carbonyl)-pyridin-2-yl]-phenyl}-propyl)-amide (HJC-1-59); Propane-2-sulfonic acid (2-{4'-[2-(2-oxo-pyrrolidin-1-yl)-ethyl]-biphenyl-4-yl}-propyl)amide (HJC-1-73); Propane-2-sulfonic acid {2-[4-(5-nitro-indol-1-yl)-phenyl]-propyl}amide (HJC-1-79); Propane-2-sulfonic acid {2-[4-(5-amino-indol-1-yl)-phenyl]-propyl}amide (HJC-1-86); Propane-2-sulfonic acid (2-{4-[5-(piperidine-1-carbonyl)-indazol-1-yl]-phenyl}-propyl)-amide (HJC-2-8); Propane-2-sulfonic acid (2-{4-[5-(pyrrolidine-1-carbonyl)-indol-1-yl]-phenyl}-propyl)amide (HJC-2-10); Propane-2-sulfonic acid (2-{4-[5-(4-methyl-piperazine-1-carbonyl)-indol-1-yl]-phenyl}-propyl)amide (HJC-2-22); Propane-2-sulfonic acid [2-(4-pyrrolo[2,3-b]pyridin-1-yl-phenyl)-propyl]amide (HJC-2-28); Propane-2-sulfonic acid [2-(4-pyrrolo[3,2-b]pyridin-1-yl-phenyl)-propyl]amide (HJC-2-29); Propane-2-sulfonic acid [2-(4-pyrrolo[3,2-c]pyridin-1-yl-phenyl)-propyl]amide (HJC-2-31); Propane-2-sulfonic acid [2-(4-pyrrolo[2,3-c]pyridin-1-yl-phenyl)-propyl]amide (HJC-2-32); Propane-2-sulfonic acid (2-{4-[5-(piperazine-1-carbonyl)-indol-1-yl]-phenyl}-propyl)amide (HJC-2-37); Propane-2-sulfonic acid {2-[4-(5-cyano-indol-1-yl)-phenyl]-propyl}amide (HJC-2-35); Propane-2-sulfonic acid [2-(4-indol-1-yl-phenyl)-propyl]amide (HJC-2-46); Pyridine-2-carboxylic acid (1-{4-[1-methyl-2-(propane-2-sulfonylamino)-ethyl]-phenyl}-1H-indol-5-yl)amide (HJC-2-48); Propane-2-sulfonic acid (2-{4-[5-(4-methanesulfonyl-piperazine-1-carbonyl)-indol-1-yl]-phenyl}-propyl)amide (HJC-2-67); Propane-2-sulfonic acid (2-{4-[5-(4-acetyl-piperazine-1-carbonyl)-indol-1-yl]-phenyl}-propyl)amide (HJC-2-68); Propane-2-sulfonic acid (2-{4-[2-(piperidine-1-carbonyl)-pyridin-4-yl]-phenyl}-propyl)-amide (HJC-2-69); or Propane-2-sulfonic acid (2-{4-[5-(pyrrolidine-1-carbonyl)-pyridin-2-yl]-phenyl}-propyl)-amide (HJC-2-70). In a further aspect the neuroprotective compound is Propane-2-sulfonic acid (2-{4-[5-(piperidine-1-carbonyl)-indol-1-yl]-phenyl}-propyl)amide (HJC-1-24) or Propane-2-sulfonic acid (2-{4-[5-(piperidine-1-carbonyl)-pyridin-2-yl]-phenyl}-propyl)-amide (HJC-1-59).

Certain embodiments are directed to methods of treating pain comprising administering a compound described herein. In certain aspects the compound is selected from Propane-2-sulfonic acid (2-{4-[2-(pyrrolidine-1-carbonyl)-pyridin-4-yl]-phenyl}-propyl)-amide (HJC-1-22); Propane-2-sulfonic acid (2-{4-[5-(piperidine-1-carbonyl)-indol-1-yl]-phenyl}-propyl)amide (HJC-1-24); Propane-2-sulfonic acid (2-{4-[5-(piperidine-1-carbonyl)-pyridin-2-yl]-phenyl}-propyl)-amide (HJC-1-59); Propane-2-sulfonic acid (2-{4'-[2-(2-oxo-pyrrolidin-1-yl)-ethyl]-biphenyl-4-yl}-propyl)amide (HJC-1-73); Propane-2-sulfonic acid {2-[4-(5-nitro-indol-1-yl)-phenyl]-propyl}amide (HJC-1-79); Propane-2-sulfonic acid {2-[4-(5-amino-indol-1-yl)-phenyl]-propyl}amide (HJC-1-86); Propane-2-sulfonic acid (2-{4-[5-(piperidine-1-carbonyl)-indazol-1-yl]-phenyl}-propyl)-amide (HJC-2-8); Propane-2-sulfonic acid (2-{4-[5-(pyrrolidine-1-carbonyl)-indol-1-yl]-phenyl}-propyl)amide (HJC-2-10); Propane-2-sulfonic acid (2-{4-[5-(4-methyl-piperazine-1-carbonyl)-indol-1-yl]-phenyl}-propyl)amide (HJC-2-22); Propane-2-sulfonic acid [2-(4-pyrrolo[2,3-b]pyridin-1-yl-phenyl)-propyl]amide (HJC-2-28); Propane-2-sulfonic acid [2-(4-pyrrolo[3,2-b]pyridin-1-yl-phenyl)-propyl]amide (HJC-2-29); Propane-2-sulfonic acid [2-(4-pyrrolo[3,2-c]pyridin-1-yl-phenyl)-propyl]amide (HJC-2-31); Propane-2-sulfonic acid [2-(4-pyrrolo[2,3-c]pyridin-1-yl-phenyl)-propyl]amide (HJC-2-32); Propane-2-sulfonic acid (2-{4-[5-(piperazine-1-carbonyl)-indol-1-yl]-phenyl}-propyl)amide (HJC-2-37); Propane-2-sulfonic acid {2-[4-(5-cyano-indol-1-yl)-phenyl]-propyl}amide (HJC-2-35); Propane-2-sulfonic acid [2-(4-indol-1-yl-phenyl)-propyl]amide (HJC-2-46); Pyridine-2-carboxylic acid (1-{4-[1-methyl-2-(propane-2-sulfonylamino)-ethyl]-phenyl}-1H-indol-5-yl)amide (HJC-2-48); Propane-2-sulfonic acid (2-{4-[5-(4-methanesulfonyl-piperazine-1-carbonyl)-indol-1-yl]-phenyl}-propyl)amide (HJC-2-67); Propane-2-sulfonic acid (2-{4-[5-(4-acetyl-piperazine-1-carbonyl)-indol-1-yl]-phenyl}-propyl)amide (HJC-2-68); Propane-2-sulfonic acid (2-{4-[2-(piperidine-1-carbonyl)-pyridin-4-yl]-phenyl}-propyl)-amide (HJC-2-69); or Propane-2-sulfonic acid (2-{4-[5-(pyrrolidine-1-carbonyl)-pyridin-2-yl]-phenyl}-propyl)-amide (HJC-2-70). In certain aspects the compound is Propane-2-sulfonic acid (2-{4-[2-(pyrrolidine-1-carbonyl)-pyridin-4-yl]-phenyl}-propyl)-amide (HJC-1-22).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one," but it is also consistent with the meaning of "one or more," "at least one," and "one or more than one."

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

The purpose of this invention is to identify highly efficacious, potent, and specific bivalent AMPAR PAMs that will enhance glutamatergic neurotransmission. In certain aspects, the compounds can prevent the effects of phencyclidine (PCP), a selective NMDA open channel blocker on developmental neuroapoptosis. This new class of highly potent and specific AMPAR PAMs having better druglike properties has been identified for preventing neuroapoptosis in a highly relevant model of human neuronal development. Such results have an important positive impact and translational value, because the newly identified AMPAR PAMs will help compensate for diminished excitatory neurotransmission in the treatment of human cognitive deficit diseases, including schizophrenia and Alzheimer's.

Figure 1:
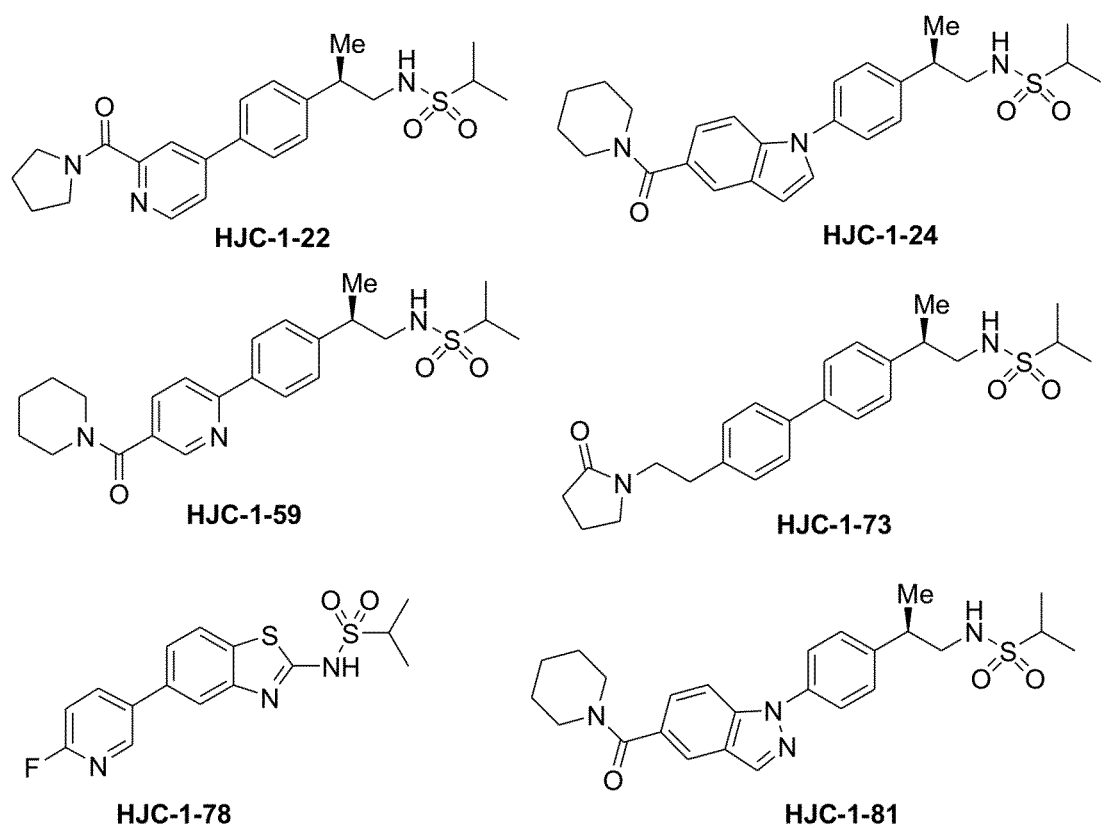
FIG. 1 Structures of Asymmetric Bivalent AMPAR PAMs.

The inventors have designed and chemically synthesized a class of new bivalent AMPAR ligands (see examples in Table 1). Preliminary studies identified two bivalent AMPAR compounds HJC-1-22 and HJC-1-24 (FIG. 1) that potently modulate the effect of AMPA on PCP-induced caspase-3 activity at a low concentration (i.e. $IC_{50}$=15 and 5 nM, respectively, FIG. 2B). The neuroprotective effect of (±)APMA on PCP-induced caspase-3 activities was potentiated by cyclothiazide (CTZ) and aniracetam, two existing AMPAR ligands (approximate $IC_{50}$ 1-3 µM, FIG. 2A for CTZ).

Figures 2A, 2B:
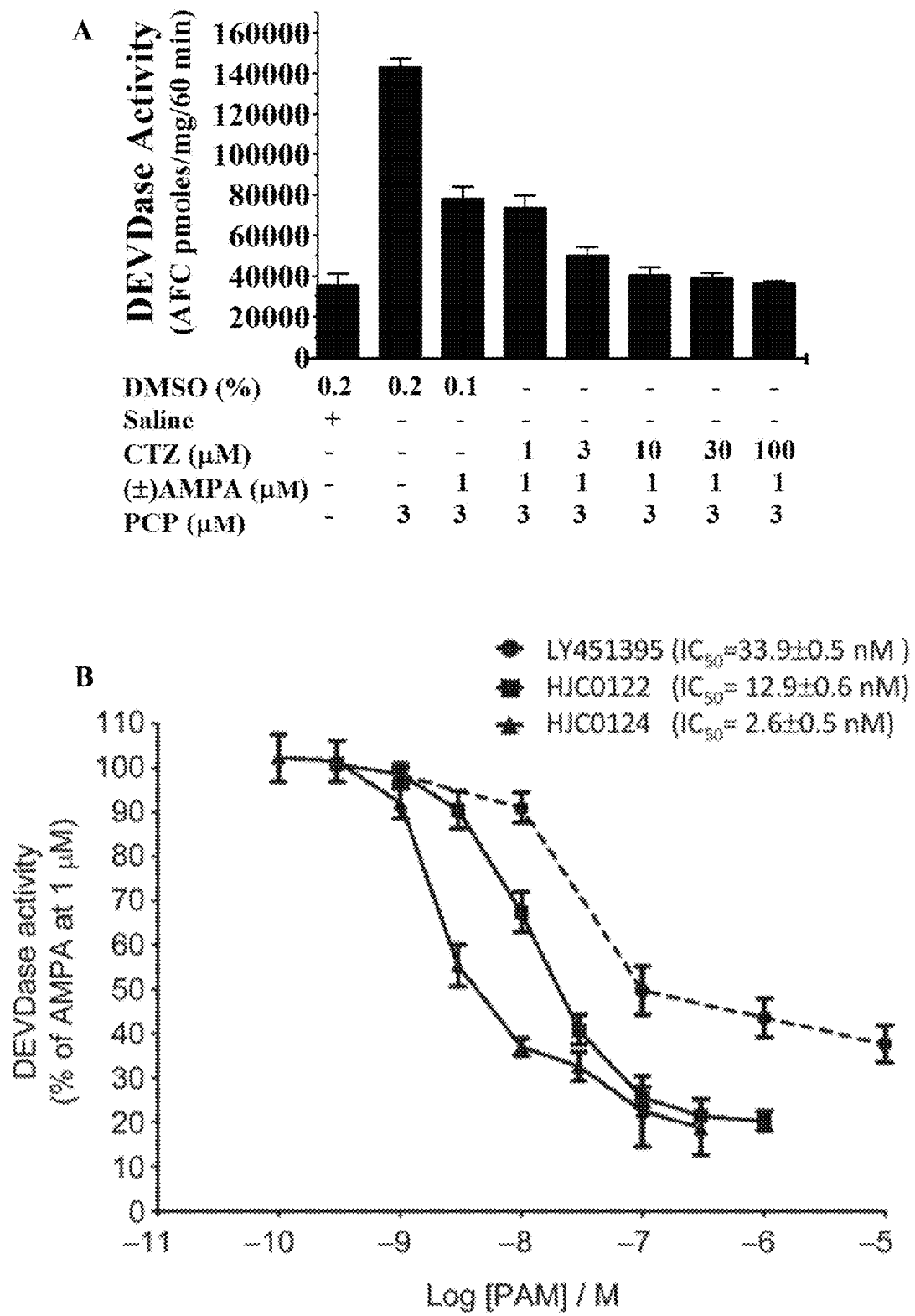
FIGS. 2A-2B (A) Cyclothiazide (CTZ) modulated effect of (±) AMPA (1 µM) on PCP (3 µM)-induced caspase-3 activity in a concentration-dependent fashion. (B) HJC0122 and HJC0124 modulated the effect of AMPA (1 mm) on caspase-3 activity induced by phencyclidine (PCP) at 3 mm in a concentration-dependent fashion and displayed more potent activity than LY451395 (currently in phase II human clinical trials).
Figure 3:
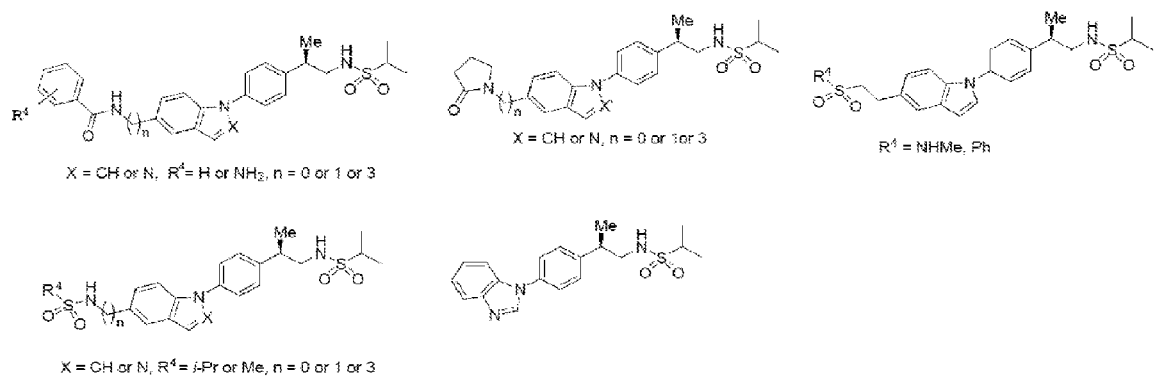
FIG. 3 Structures of novel AMPAR PAMs.
Figure 4:
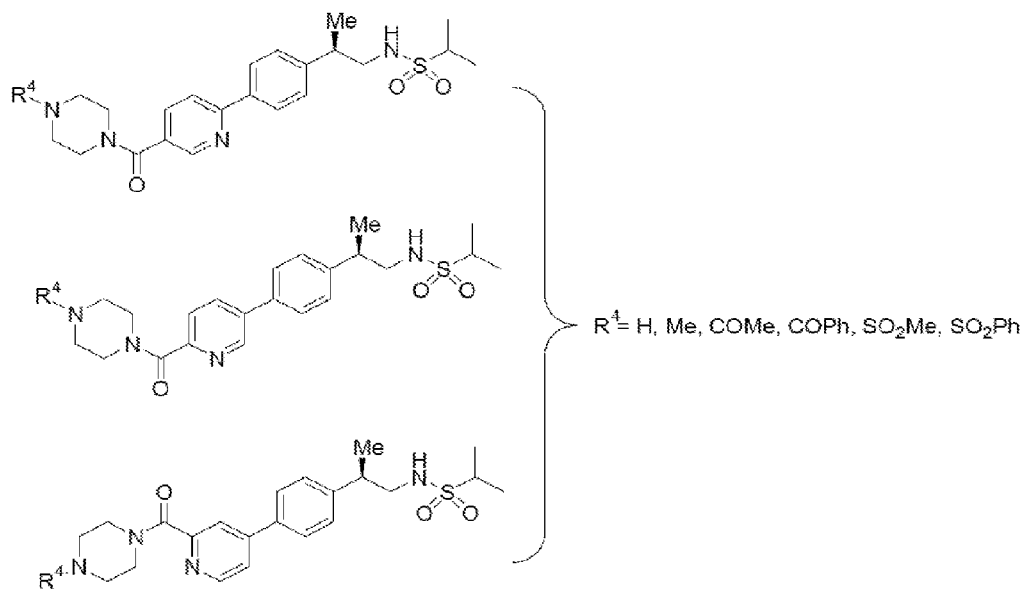
FIG. 4 Additional structures of AMPAR PAMs.
Figure 5:
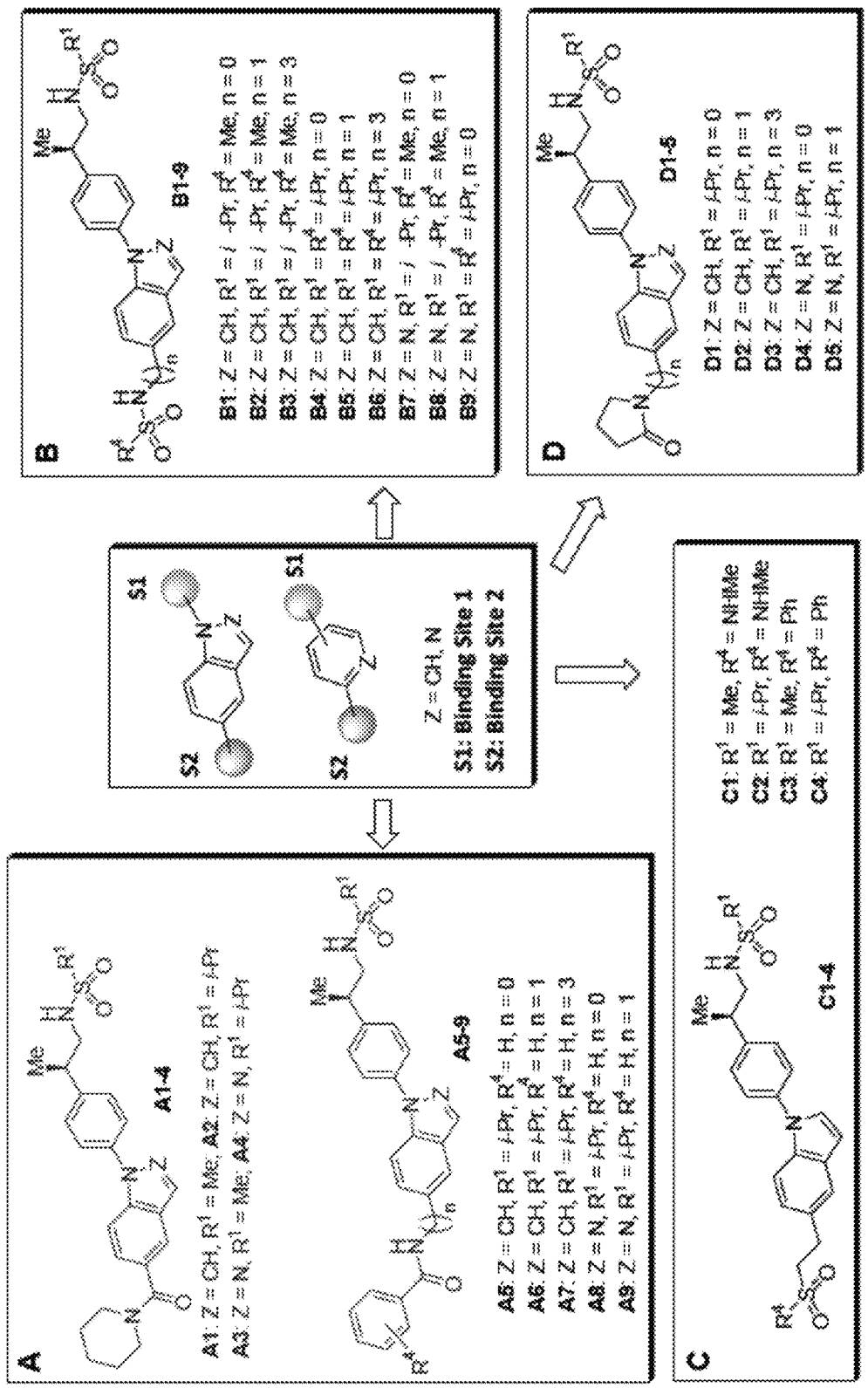
FIG. 5 Illustration of rational drug design and AMPAR PAMs targeting two binding sites.
Figure 6:
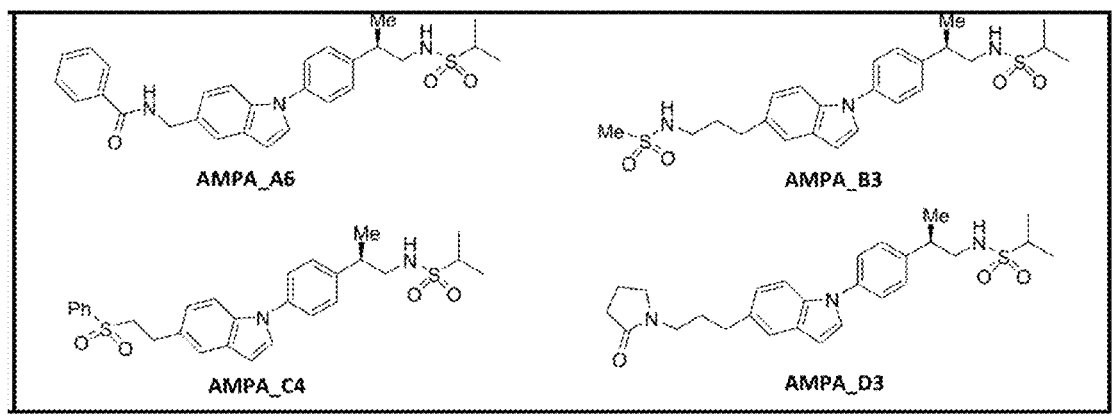
FIG. 6 AMPAR PAMs targeting the dimeric binding sites were designed using docking algorithms. The molecular energies with the MMFF94 force field were minimized, and the small molecules were allowed to flex during the orientation search up to a maximum of 6,000 conformations. The scores including both electrostatic and vDW components predict that a good number of newly designed ligands from three series such as AMPA_A6, AMPA_B3, AMPA_C4, and AMPA_D3 have excellent binding to the pocket and AMPA_B3 stands out with the best score and binding mode.
Figures 7A, 7B, 7C, 7D, 7E:
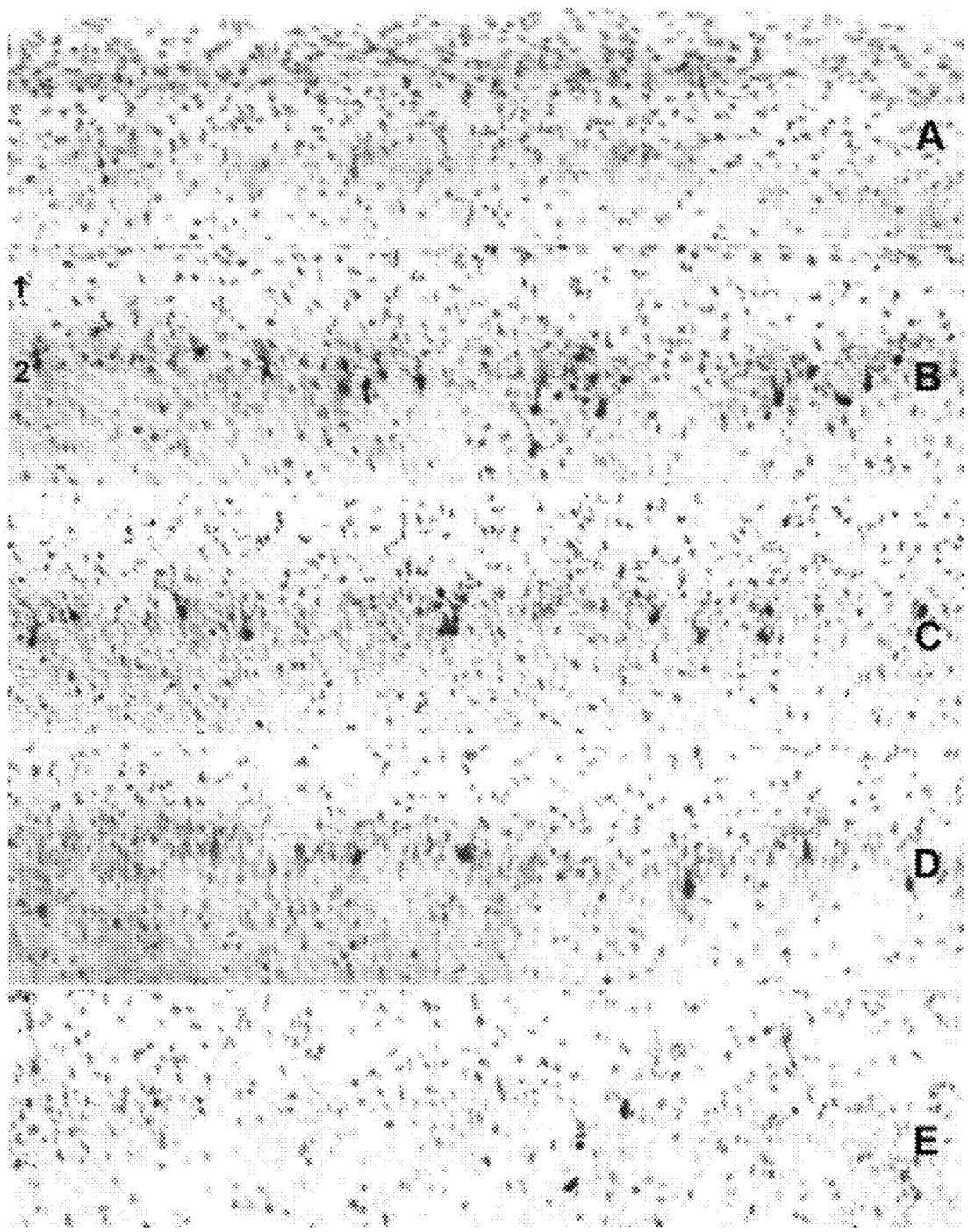
FIGS. 7A-7E HJC-1-22 has displayed promising preventive effect in vivo and significantly reduced PCP-induced cleaved caspase-3 immunoreactive neurons in frontal cortex (M2/1) of PND7 rats in a dose-dependent fashion (FIG. 7). Cleaved caspase-3 immunoreactive neurons, 8 hrs on PND7 after Saline (A) or PCP (10 mg/kg, sc, B-E) without (A-B) or with (C-E) pretreatment (30 min prior to PCP) of HJC-1-22 (C, 0.1 mg/kg; D, 1 mg/kg; E, 10 mg/kg, sc) were shown. HJC-1-22 at 10 mg/kg was found to prevent 85% of PCP (10 mg/kg)-induced caspase-3 activation in frontal cortex of PND7 rats (FIG. 7E).

HJC-1-22 significantly potentiated the effect of (±)AMPA and significantly reduced PCP-induced caspase-3 activities in organotypic slices with an $IC_{50}$ of 15 nM (FIG. 2B). In addition, HJC-1-22 has displayed promising preventive effect in vivo and significantly reduced PCP-induced cleaved caspase-3 immunoreactive neurons in frontal cortex (M2/1) of PND7 rats in a dose-dependent fashion. HJC-1-22 at 10 mg/kg was found to prevent 85% of PCP (10 mg/kg)-induced caspase-3 activation in frontal cortex of PND7 rats (FIG. 7).

As shown in FIG. 2B, the newly designed and synthesized bivalent ligand HJC-1-24 significantly modulated (±)AMPA effect on PCP-induced caspase-3 activities with an $IC_{50}$ of 5 nM, which is at least 200-fold more potent than CTZ.

Figure 8:
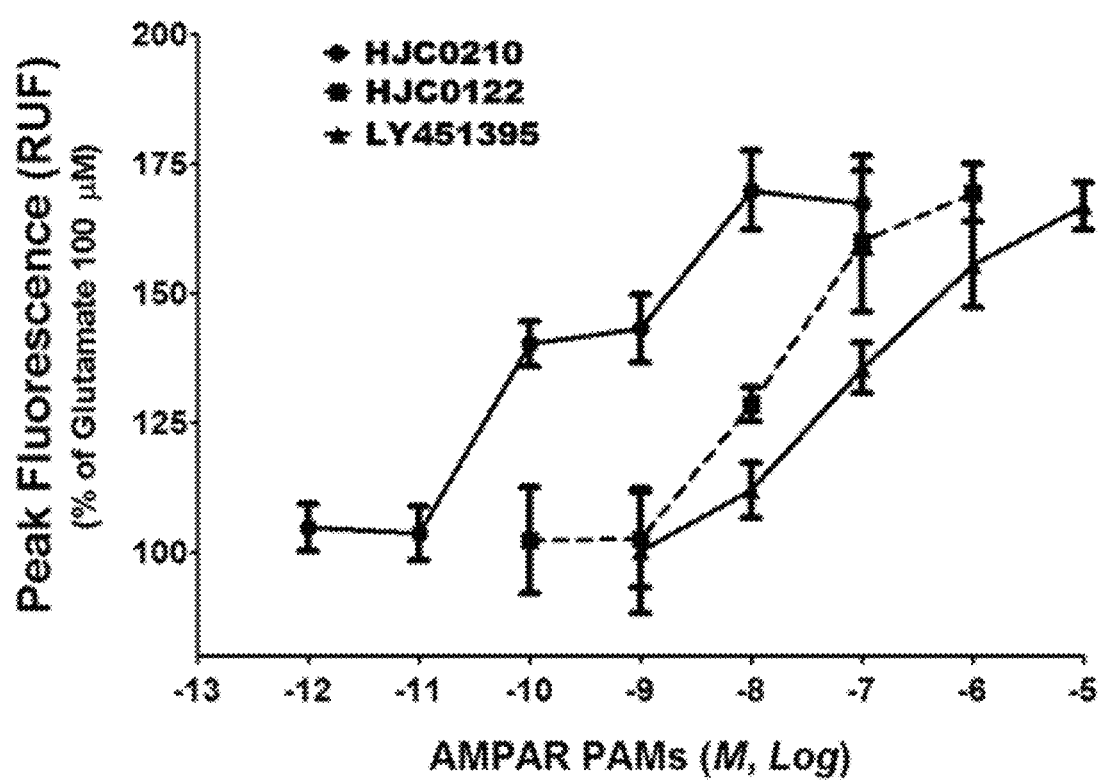
FIG. 8 HJC0210, HJC0122 and LY451395 enhanced glutamate (100 µM)-evoked calcium influx in a concentration-dependent manner in DIV9 dissociated rat forebrain neurons cultured on PND1 (postnatal day 1). Effects of selected AMPA PAMs on Glutamate (100 µM)-evoked $Ca^{2+}$ influx are shown in Table 2.

As shown in FIG. 8, HJC0210, HJC0122 and LY451395 enhanced glutamate (100 µM)-evoked calcium influx in a concentration-dependent manner in DIV9 dissociated rat forebrain neurons cultured on PND1 (postnatal day 1). Effects of selected AMPA PAMs on Glutamate (100 µM)- evoked Ca$^{2+}$ influx have demonstrated nanomolar to picomolar potency with good E$_{max}$ (Table 2).

TABLE 2

Effects of AMPA PAMs on Glutamate (100 μM)-evoked Ca$^{2+}$ influx:

| Compound | Structure | pEC$_{50}$ (-logEC$_{50}$) | EC$_{50}$ (nM) | E$_{max}$ (%) |
|---|---|---|---|---|
| HJC0122 | 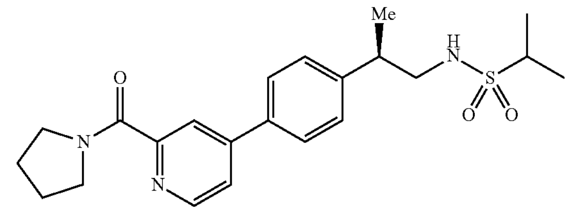 [SMILES: CC(C)S(=O)(=O)NC[C@H](C)c1ccc(-c2ccnc(C(=O)N3CCCC3)c2)cc1] | 8.28 | 6.53 | 170.0 |
| HJC0173 | 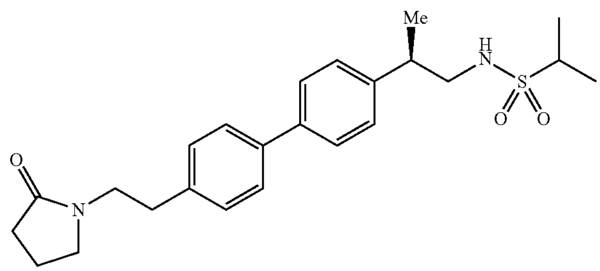 [SMILES: CC(C)S(=O)(=O)NC[C@H](C)c1ccc(-c2ccc(CCN3CCCC3=O)cc2)cc1] | 8.39 | 4.02 | 127.1 |
| HJC0210 | 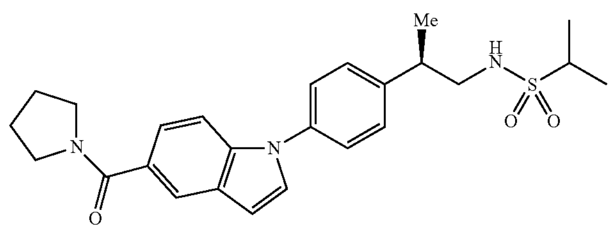 [SMILES: CC(C)S(=O)(=O)NC[C@H](C)c1ccc(-n2ccc3cc(C(=O)N4CCCC4)ccc32)cc1] | 10.21 | 0.06 | 157.5 |
| HJC0229 | 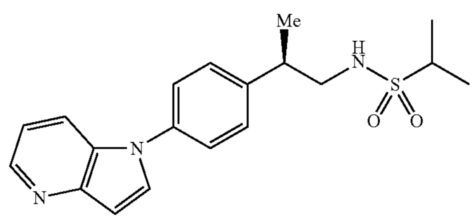 [SMILES: CC(C)S(=O)(=O)NC[C@H](C)c1ccc(-n2ccc3ncccc32)cc1] | 8.06 | 8.76 | 168.9 |

Additional embodiments are directed to methods of neuroprotection or pain management.

Certain embodiments are directed to neuroprotective methods, and more specifically to methods and compounds for prevention of damage to cells of the mammalian central and peripheral nervous system resulting from injury, trauma, surgery or acute or chronic disease processes.

In certain aspects methods provide for neuroprotection; for inhibiting cell degeneration or cell death; for treatment or prophylaxis of a neurodegenerative disease; or for ameliorating the cytotoxic effect of a compound (for example, a excitatory amino acid such as glutamate; a toxin; or a prophylactic or therapeutic compound that exerts a cytotoxic side effect) in a subject in need thereof, by administering to the subject an effective amount of a compound described herein, or it's pharmaceutically acceptable salt or ester either alone or in combination with another medication along with a pharmaceutically acceptable excipient. In various embodiments, the methods of the invention include protection against excitotoxicity, for example glutamate excitotoxicity.

In various embodiments, the subject, for example, a human, may be suffering from neural insult or injury; or may be suffering from a condition selected from substance abuse, trauma, stroke, ischemia, Huntington's disease, Alzheimer's disease, Parkinson's disease, prion disease, variant Creutzfeld-Jakob disease, amyotrophic or hypoglycemic encephalopathy; or may be undergoing surgery or other intervention. The subject may have a pre-existing condition that would benefit by neuroprotection or the patient may be treated to reduce deleterious effects of a concomitant or subsequent neural injury, such as may occur during surgery or other intervention.

Neuroprotection was demonstrated by infusing compounds into 4 mice each, at 10 μM, and the density of BrdU+ cells/mm3 dentate gyms were determined by quantifying every fifth section throughout the hippocampus. HJC0120=173.3+/−12.7×10E06 BrdU+ cells/mm3 dentate gyms; HJC0122=87.7+/−2.7×10E06 Brdu+ cells/mm3 dentate gyms; HJC0124=120.4+/−4.1×10E06 BrdU+ cells/mm3 dentate gyms; HJC0159=176.7+/−14.9×10E06 BrdU+ cells/mm3 dentate gyms; HJC0 210=100.5+/−7.3×10E06 BrdU+ cells/mm3 dentate gyms; HJC0 229=151.82+/−21.38×10E06

BrdU+ cells/mm3 dentate gyms in this one, if an outlier is eliminated, the value is: 169.7+/−14.4×10E06 BrdU+ cells/mm3 dentate gyms; and HJC0173=151.42+/−18.2×10E06 BrdU+ cells/mm3 dentate gyms.

Opioids (e.g., morphine) are highly efficacious analgesic drugs. Morphine is routinely used to reduce pain in humans. For example, surgery patients are typically instructed to take 5 to 10 mg of morphine per person to alleviate pain caused by the surgical procedure. In some cases, patients suffering from extreme pain (e.g., burn victims or cancer patients) are instructed to take higher doses of morphine. However, repeated use of these drugs leads to the development of tolerance and dependence, thereby limiting their effectiveness and usage. Certain embodiments are directed to methods of reducing the development of tolerance or dependence on opioids and thus managing pain by administering. A compound described herein. In certain aspects compounds described herein are administered in conjunction with opioids.

The mechanisms underlying opioid tolerance and dependence are not entirely understood. AMPAR PAMs were tested in morphine tolerance and dependence models. AMPAR PAMs can both prevent and acutely reverse tolerance (FIG. 9 and FIG. 10). At 10 mg/kg, it partially attenuated naloxone-induced withdrawal.

I. CHEMICAL DEFINITIONS

Various chemical definitions related to AMPAR modulating compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer. In certain aspects, one, both, or the predominant enantiomer forms or isomers are all covered.

As used herein, the term "nitro" means —$NO_2$; the term "halo" or "halogen" designates —F, —Cl, —Br, or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e. unbranched) or branched carbon chain of 1, 2, 3, 4, 5, 6, 7, 8, 9, or 10 carbons, which may be fully saturated, monounsaturated, or polyunsaturated. An unsaturated alkyl group includes those having one or more carbon-carbon double bonds (alkenyl) and those having one or more carbon-carbon triple bonds (alkenyl). The groups, —$CH_3$ (Me, methyl), —$CH_2CH_3$ (Et, ethyl), —$CH_2CH_2CH_3$ (n-Pr, n-propyl), —$CH(CH_3)_2$ (iso-Pr, iso-propyl), —$CH_2CH_2CH_2CH_3$ (n-Bu, n-butyl), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, S, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Examples of cycloalkyl groups include cyclopropyl, cyclobutyl, cyclopentyl, cyclohexyl, and cycloheptyl groups. Examples of heterocyclic groups include indole, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 4-azaindole, 5-azaindole, 6-azaindole, 7-azaindole, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$ amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$ amino, alkylsulfinyl, alkylsulfonyl, arylsulfonyl, unsubstituted cycloalkyl, unsubstituted heterocyclyl, unsubstituted aryl, or unsubstituted heteroaryl. Examples of optional substituents include, but are not limited to: —OH, oxo (=O), —Cl, —F, Br, $C_{1-4}$alkyl, phenyl, benzyl, —$NH_2$, —NH($C_{1-4}$alkyl), —N($C_{1-4}$alkyl)$_2$, —NO$_2$, —S($C_{1-4}$alkyl), —SO$_2$($C_{1-4}$alkyl), —CO$_2$($C_{1-4}$alkyl), and —O($C_{1-4}$alkyl).

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

II. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Propane-2-sulfonic acid (2-phenyl-propyl)amide (HJC-1-1)

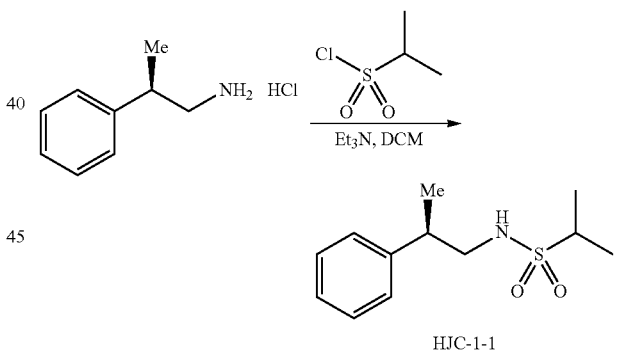

To a solution of 2-phenyl-propylamine HCl salt (1.0 g, 5.8 mmol), DMAP (35 mg, 0.3 mmol) and Et$_3$N (1.77 g, 17.5 mmol) in DCM (25 mL) was added propane-2-sulfonyl chloride (1.25 g, 8.7 mmol) dropwise at 0° C. The mixture was stirred at r.t. for 16 h, and was then concentrated under vacuum. The residue was partitioned between EtOAc (100 mL) and H$_2$O (10 mL). The organic layer was separated and washed with brine (10 mL), dried over anhydrous Na$_2$SO$_4$, filtrated and concentrated to give an oil residue. This residue was purified with silica gel column (Hexane/EtOAc=2/1 to 1/1) to obtain the desired product (1.2 g, 86%) as a pale yellow oil. $^1$H NMR (600 MHz, CDCl$_3$) δ 7.30-7.32 (m, 2H), 7.18-7.24 (m, 3H), 3.90-3.94 (m, 1H), 3.30-3.35 (m, 1H), 3.18-3.22 (m, 1H), 2.99-3.04 (m, 1H), 2.91-2.95 (m, 1H), 1.27 (d, 3H, J=7.2 Hz), 1.25 (d, H, J=7.8 Hz), 1.22 (d, 1H, J=7.2 Hz).

Example 2

Propane-2-sulfonic acid [2-(4-iodo-phenyl)-propyl] amide (HJC-1-2)

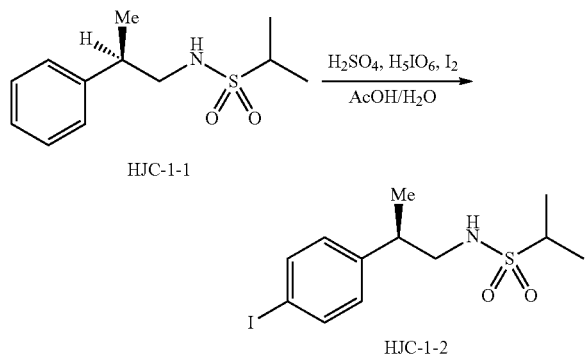

To a solution of HJC-1-1 (900 mg, 3.73 mmol) in AcOH/H$_2$O (5 mL/1 mL) was added concentrated H$_2$SO$_4$ (387 mg, 3.95 mmol) dropwise at 0° C. Add H$_5$IO$_6$ (212 mg, 0.93 mmol), followed by iodine (473 mg, 1.86 mmol) to this solution. The mixture was stirred at 60° C. for 3 h and then was diluted with EtOAc (50 mL) and washed with 10% NaHSO$_3$/H2O (20 mL). The organic layer was separated and washed with sat. NaHCO$_3$ (20 mL) and then brine (10 mL), dried over anhydrous Na$_2$SO$_4$, filtrated and concentrated to give an oil residue. This residue was purified with silica gel column (Hexane/EtOAc=20/1) to obtain the desired product (724 mg, 53%) as a white solid. $^1$H NMR (600 MHz, CDCl$_3$) δ 7.64 (d, 2H, J=8.4 Hz), 6.95 (d, 2H, J=8.4 Hz), 3.80-3.84 (m, 1H), 3.28-3.31 (m, 1H), 3.14-3.18 (m, 1H), 3.02-3.05 (m, 1H), 2.88-2.91 (m, 1H), 1.28 (d, 3H, J=6.6 Hz), 1.25 (d, 6H, J=6.6 Hz).

Example 3

Propane-2-Sulfonic acid {2-[4-(4,4,5,5-tetramethyl-[1,3,2]Dioxaborolan-2-yl-phenyl]-propyl}amide (HJC-1-5)

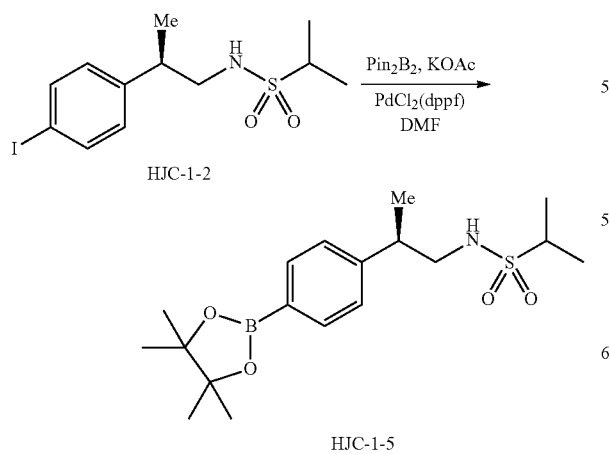

To a solution of HJC-1-2 (180 mg, 0.49 mmol) and Pin$_2$B$_2$ (137 mg, 0.54 mmol) in DMF (10 mL) was added KOAc (144 mg, 1.47 mmol) and then Pd(dppf)Cl$_2$ (12 mg, 0.015 mmol). The resulting mixture was deoxygenated via five vacuum/N$_2$-refill cycles. The mixture was stirred at 80° C. for 18 h, and was then concentrated under vacuum. TLC indicated that the starting material was gone. The mixture was diluted with EtOAc (50 mL) and washed with water (10 mL). The organic layer was separated and dried over anhydrous Na$_2$SO$_4$. The solution was concentrated to give a crude product, which was purified with silica gel column (Hexane/EtOAc=3/1 to 1/1) to obtain HJC-1-5 (130 mg, 72%) as a white solid. $^1$H NMR (600 MHz, CDCl$_3$) δ 7.76 (d, 2H, J=7.2 Hz), 7.19 (d, 2H, J=7.2 Hz), 3.72-3.78 (m, 1H), 3.32-3.37 (m, 1H), 3.18-3.22 (m, 1H), 3.01-3.04 (m, 1H), 2.94-2.97 (m, 1H), 1.32 (s, 12H), 1.26-1.27 (m, 6H), 1.19-1.22 (m, 3H).

Example 4

4-Iodo-pyridin-2-yl)-pyrrolidin-1-yl-methanone (HJC-1-8

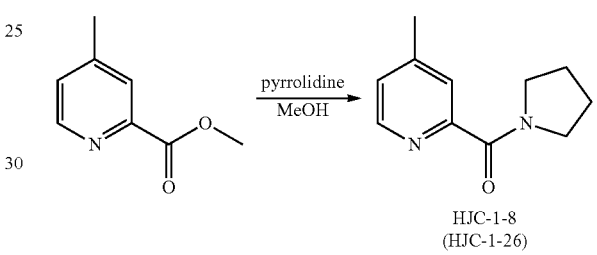

To a solution of 4-iodo-pyridine-2-carboxylic acid methyl ester (260 mg, 1.0 mmol) in 1 mL of MeOH was added 1 mL of pyrrolidine. The resulting mixture was stirred at r.t. for 18 h. TLC indicated that the starting material was gone. The mixture was diluted with EtOAc (50 mL) and washed with water (20 mL). The organic layer was separated and washed with 0.5 N HCl (20 mL) and then brine (10 mL). After drying over anhydrous Na$_2$SO$_4$, the solution was concentrated to give a white solid (280 mg, 93%). $^1$H NMR (600 MHz, CDCl$_3$) δ 8.24 (s, 1H), 8.22 (d, 1H, J=6.6 Hz), 7.71 (d, 1H, J=6.6 Hz), 3.68-3.71 (m, 2H), 3.67-3.69 (m, 2H), 1.81-1.88 (m, 4H).

Example 5

Propane-2-sulfonic acid (2-{4-[2-(pyrrolidine-1-carbonyl)-pyridin-4-yl]phenyl}-propyl)-amide (HJC-1-22)

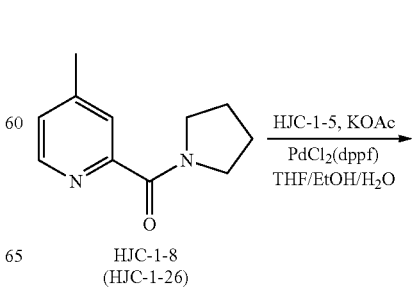

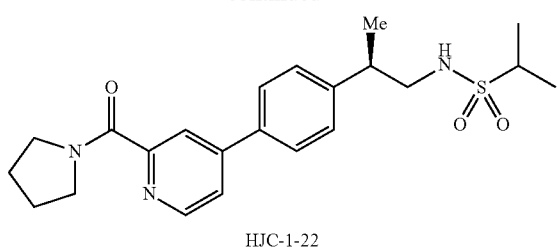

HJC-1-22

To a solution of HJC-1-5 (56 mg, 0.15 mmol) and HJC-1-8 (51 mg, 0.17 mmol) in THF/EtOH/H₂O (2 mL/2 mL/2 mL) was added KOAc (45 mg, 0.46 mmol) and then Pd(dppf)Cl₂ (6 mg, 0.008 mmol). The resulting mixture was deoxygenated via five vacuum/N₂-refill cycles. The mixture was stirred at 80° C. for 18 h, and was then concentrated under vacuum. The residue was partitioned between EtOAc (50 mL) and H₂O (20 mL). The organic layer was separated and washed with brine (10 mL), dried over anhydrous Na₂SO₄, filtrated and concentrated to give an oil residue. This residue was purified with silica gel column (Hexane/EtOAc=1/2) to obtain HJC-1-22 (30 mg, 47%) as a pale yellow oil. ¹H NMR (600 MHz, CDCl₃) δ 8.60 (d, 1H, J=4.8 Hz), 8.03 (s, 1H), 7.64 (d, 2H, J=7.2 Hz), 7.53 (d, 1H, J=4.8 Hz), 7.34 (d, 2H, J=7.2 Hz), 4.15-4.19 (m, 1H), 3.76-3.79 (m, 2H), 3.70-3.73 (m, 2H), 3.35-3.40 (m, 1H), 3.25-3.29 (m, 1H), 3.03-3.09 (m, 2H), 1.91-1.95 (m, 4H), 1.33 (d, 3H, J=6.6 Hz), 1.30 (d, 3H, J=7.2 Hz), 1.26 (d, 3H, J=6.6 Hz). ¹³C NMR (150 MHz, CDCl₃) δ 166.7, 155.3, 148.8, 148.7, 144.8, 136.5, 128.3, 127.6, 122.3, 121.6, 53.6, 50.3, 49.3, 47.0, 40.8, 26.7, 24.2, 19.1, 16.7, 16.6.

Example 6

1H-Indol-5-yl)-piperidin-1-yl-methanone (HJC-1-21

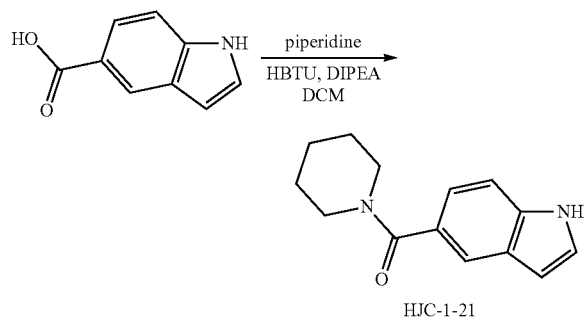

HJC-1-21

To a solution of 1H-Indole-5-carboxylic acid (323 mg, 2.0 mmol) in 10 mL of DCM was added DIPEA (1.29 g, 10.0 mmol) and piperidine (852 mg, 10.0 mmol). HBTU (1.14 g, 3.0 mmol) was added at 0° C. The resulting mixture was stirred at r.t. for 18 h. TLC indicated that the starting material was gone. The mixture was diluted with DCM (100 mL) and washed with water (30 mL). The organic layer was separated and dried over anhydrous Na₂SO₄. The solution was concentrated to give a crude product, which was purified with silica gel column (DCM/EtOAc/Hexane=1/1/1) to obtain HJC-1-21 (410 mg, 90%) as a white solid. ¹H NMR (600 MHz, CDCl₃) δ 8.85 (s, 1H), 7.70 (s, 1H), 7.28-7.34 (m, 1H), 7.19-7.24 (m, 2H), 6.54-6.56 (m, 1H), 3.46-3.74 (m, 4H), 1.48-1.77 (m, 6H).

Example 7

Propane-2-sulfonic acid (2-{4-[5-(piperidine-1-carbonyl)-indol-1-yl]-phenyl}-propyl)amide (HJC-1-24)

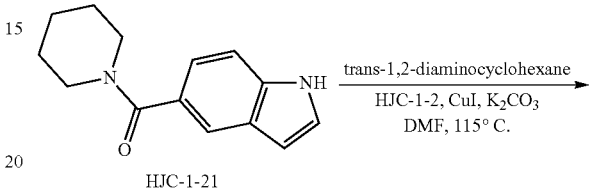

HJC-1-21

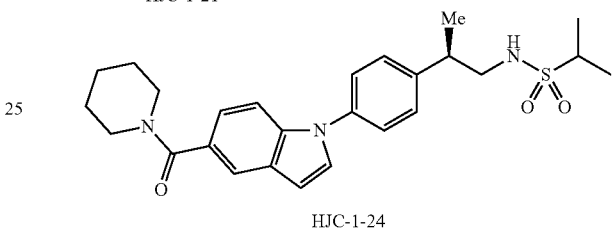

HJC-1-24

To a solution of HJC-1-2 (176 mg, 0.48 mmol) and HJC-1-21 (120 mg, 0.53 mmol) in DMF (10 mL) was added K₂CO₃ (133 mg, 0.96 mmol), trans-1,2-diaminocyclohexane (11 mg, 0.096 mmol) and then CuI (18 mg, 0.096 mmol). The resulting mixture was deoxygenated via five vacuum/N₂-refill cycles. The mixture was stirred at 115° C. for 18 h. The mixture was partitioned between EtOAc (100 mL) and H₂O (30 mL). The organic layer was separated and washed with brine (10 mL), dried over anhydrous Na₂SO₄, filtrated and concentrated to give an oil residue. This residue was purified with silica gel column (Hexane/EtOAc=1/1) to obtain HJC-1-24 (40 mg, 18%) as a pale yellow oil. ¹H NMR (600 MHz, CDCl₃) δ 7.75 (s, 1H), 7.53 (d, 1H, J=8.4 Hz), 7.46 (d, 2H, J=8.4 Hz), 7.37 (d, 2H, J=7.8 Hz), 7.35 (d, 1H, J=3.6 Hz), 7.28 (dd, 1H, J=1.8, 8.4 Hz), 4.04-4.06 (m, 1H), 3.47-3.75 (m, 4H), 3.37-3.42 (m, 1H), 3.27-3.31 (m, 1H), 3.04-3.12 (m, 2H), 3.03-3.09 (m, 2H), 1.52-1.69 (m, 6H), 1.36 (d, 3H, J=7.2 Hz), 1.33 (d, 3H, J=7.2 Hz), 1.30 (d, 3H, J=6.6 Hz). ¹³C NMR (150 MHz, CDCl₃) δ 171.6, 142.0, 138.5, 136.3, 139.0, 128.9, 128.8, 128.7, 124.9, 121.9, 120.5, 110.5, 104.3, 53.7, 50.5, 40.7, 24.9, 19.2, 16.8, 16.7.

Example 8

6-Bromo-pyridin-3-yl)-piperidin-1-yl-methanone (HJC-1-55

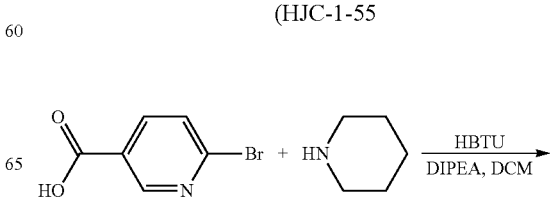

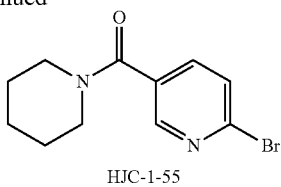

HJC-1-55

To a solution of 6-bromo-nicotinic acid (404 mg, 2.0 mmol) in 15 mL of DCM was added DIPEA (1.29 g, 10.0 mmol) and piperidine (852 mg, 10.0 mmol). HBTU (1.14 g, 3.0 mmol) was added at 0° C. The resulting mixture was stirred at r.t. for 18 h. TLC indicated that the starting material was gone. The mixture was diluted with DCM (100 mL) and washed with water (30 mL). The organic layer was separated and dried over anhydrous $Na_2SO_4$. The solution was concentrated to give a crude product. This residue was purified with silica gel column (Hexane/EtOAc=3/1) to obtain HJC-1-55 (540 mg, 100%) as a white solid. $^1$H NMR (600 MHz, CDCl$_3$) δ 8.41 (s, 1H), 7.60 (d, 1H, J=8.4 Hz), 7.54 (d, 1H, J=7.8 Hz), 3.67-3.71 (m, 2H), 3.31-3.35 (m, 2H), 1.63-1.70 (m, 4H), 1.49-1.55 (m, 2H).

Example 9

Propane-2-sulfonic acid (2-{4-[5-(piperidine-1-carbonyl)-pyridin-2-yl]phenyl}-propyl)-amide (HJC-1-59)

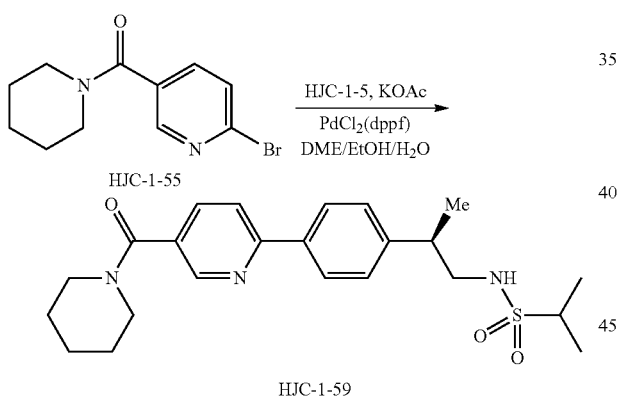

To a solution of HJC-1-5 (100 mg, 0.27 mmol) and HJC-1-55 (81 mg, 0.30 mmol) in DME/EtOH/H$_2$O (3 mL/3 mL/3 mL) was added KOAc (80 mg, 0.82 mmol) and then Pd(dppf)Cl$_2$ (17 mg, 0.02 mmol). The resulting mixture was deoxygenated via five vacuum/N$_2$-refill cycles. The mixture was stirred at 80° C. for 18 h. The mixture was concentrated under vacuum. The residue was partitioned between EtOAc (50 mL) and H$_2$O (10 mL). The organic layer was separated and washed with brine (10 mL), dried over anhydrous Na$_2$SO$_4$, filtrated and concentrated to give an oil residue. This residue was purified with silica gel column (Hexane/EtOAc=3/1 to 1/1) to obtain HJC-1-59 (35 mg, 60%) as a colorless oil and some HJC-1-5 (50 mg) as recovered material. $^1$H NMR (600 MHz, CDCl$_3$) δ 8.70 (s, 1H), 7.96 (d, 2H, J=7.8 Hz), 7.81 (d, 1H, J=6.6 Hz), 7.74 (d, 1H, J=7.8 Hz), 7.33 (d, 2H, J=7.8 Hz), 4.10-4.12 (m, 1H), 3.70-3.75 (m, 2H), 3.39-3.42 (m, 2H), 3.34-3.39 (m, 1H), 3.24-3.27 (m, 1H), 3.02-3.07 (m, 2H), 1.65-1.70 (m, 4H), 1.54-1.58 (m, 2H), 1.32 (d, 3H, J=7.2 Hz), 1.28 (d, 3H, J=7.2 Hz), 1.24 (d, 3H, J=6.6 Hz). $^{13}$C NMR (150 MHz, CDCl$_3$) δ 167.8, 157.9, 147.9, 144.8, 137.5, 136.0, 130.5, 127.9, 127.6, 120.1, 53.5, 50.3, 49.1, 40.8, 24.6, 19.1, 16.7, 16.6.

Example 10

4-Chloro-N-phenethyl-butyramide (HJC-1-48)

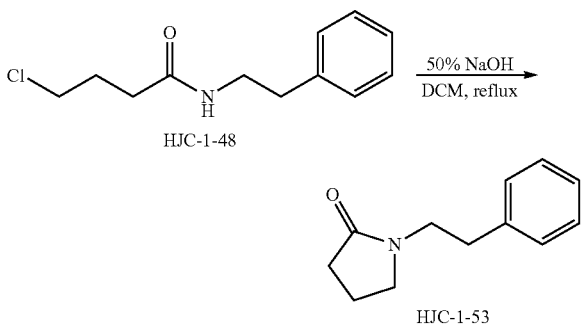

To a solution of phenethylamine (2.42 g, 20 mmol) and NaOH (0.88 g, 22 mmol) in DCM/H$_2$O (20 mL/20 mL) was added 4-chloro-butyryl chloride (2.82 g, 20 mmol) at 0° C. The resulting mixture was stirred at 0° C. for 20 min. The mixture was partitioned between DCM (20 mL) and H$_2$O (10 mL). The organic layer was separated and washed with brine (10 mL), dried over anhydrous Na$_2$SO$_4$, filtered and concentrated to give a white solid. This residue was purified with silica gel column (Hexane/EtOAc=3/1 to 1/1) to obtain HJC-1-48 (4.2 g, 93%) as a white solid. $^1$H NMR (600 MHz, CDCl$_3$) δ 7.32 (t, 2H, J=7.8 Hz), 7.23-7.26 (m, 1H), 7.20 (d, 2H, J=7.8 Hz), 5.46-5.47 (m, 1H), 3.52-3.58 (m, 4H), 2.82 (t, 2H, J=7.2 Hz), 2.31 (t, 2H, J=7.2 Hz), 2.07-2.11 (m, 2H).

Example 11

1-Phenethyl-pyrrolidin-2-one (HJC-1-53)

To a solution of HJC-1-48 (4.2 g, 18.6 mmol) in DCM/H$_2$O (20 mL/8 mL) was added (n-Bu)$_4$NBr (0.3 g, 0.9 mmol) and NaOH (3.7 g, 93.0 mmol). The resulting mixture was stirred at 100° C. for 7 h. The mixture was partitioned between EtOAc (200 mL) and H$_2$O (10 mL). The organic layer was separated and washed with brine (20 mL), dried over anhydrous Na$_2$SO$_4$, filtered and concentrated to give an oil residue. This residue was purified with silica gel column (Hexane/EtOAc=1/1 to 1/2) to obtain HJC-1-53 (4.2 g, 93%) as a pale yellow oil. $^1$H NMR (600 MHz, CDCl$_3$) δ 7.26-7.30 (m, 2H), 7.18-7.22 (m, 3H), 3.53 (t, 2H, J=7.8 Hz), 3.25 (t, 2H, J=7.2 Hz), 2.84 (t, 2H, J=7.8 Hz), 2.34 (t, 2H, J=7.8 Hz), 1.92-1.97 (m, 2H).

Example 12

1-[2-(4-Iodo-phenyl)-ethyl]pyrrolidin-2-one (HJC-1-60)

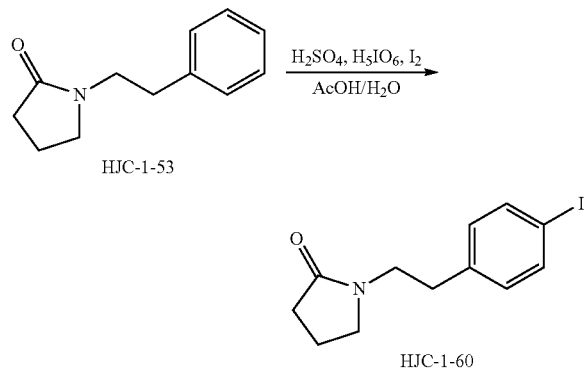

To a stirring solution of HJC-1-53 (500 mg, 2.6 mmol), water (1 mL), 95% sulfuric acid (285 mg, 2.9 mmol) and acetic acid (8 mL) was added iodine (335 mg, 1.3 mmol) and periodic acid (H$_5$IO$_6$, 150 mg, 0.7 mmol) at rt. The reaction mixture was warmed to 60° C. for 3 h. After cooling down to rt, the solution was extracted with EtOAc (80 mL) and H$_2$O (20 mL), and washed with 10% NaHSO$_3$ (20 mL), followed by 10% NaHCO$_3$ (40 mL). The organic layer was separated and washed with brine (10 mL), dried over anhydrous Na$_2$SO$_4$, filtered and concentrated to give an oil residue. This residue was purified with silica gel column (Hexane/EtOAc=1/2) to obtain HJC-1-60 (130 mg, 16%) as a pale yellow oil. $^1$H NMR (600 MHz, CDCl$_3$) δ 7.60 (d, 1H, J=7.8 Hz), 7.26-7.30 (m, 1H), 7.19-7.21 (m, 1H), 6.96 (d, 1H, J=9.0 Hz), 3.48-3.53 (m, 2H), 3.23-3.26 (m, 2H), 2.83 (t, 1H, J=7.8 Hz), 2.78 (t, 1H, J=7.8 Hz), 2.32-2.36 (m, 2H), 1.91-1.97 (m, 2H).

Example 13

Propane-2-sulfonic acid (2-{4'-[2-(2-oxo-pyrrolidin-1-yl)-ethyl]-biphenyl-4-yl}-propyl)amide (HJC-1-73)

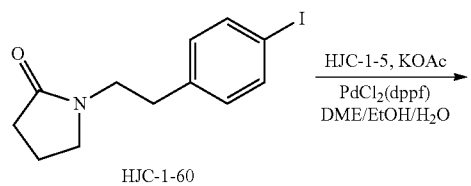

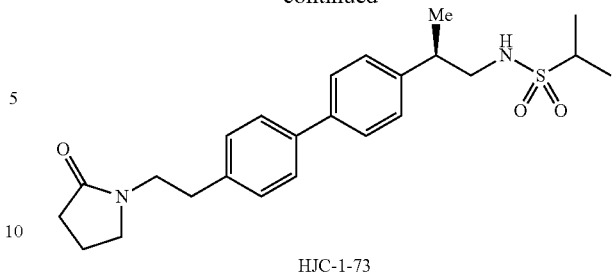

To a solution of HJC-1-5 (73 mg, 0.2 mmol) and HJC-1-60 (64 mg, 0.2 mmol) in DME/EtOH/H$_2$O (3 mL/3 mL/3 mL) was added KOAc (59 mg, 0.6 mmol) and then Pd(dppf)Cl$_2$ (17 mg, 0.02 mmol). The resulting mixture was deoxygenated via five vacuum/N$_2$-refill cycles. The mixture was stirred at 80° C. for 18 h, and was then concentrated under vacuum. The residue was partitioned between EtOAc (50 mL) and H$_2$O (10 mL). The organic layer was separated and washed with brine (10 mL), dried over anhydrous Na$_2$SO$_4$, filtered and concentrated to give an oil residue. This residue was purified with silica gel column (Hexane/EtOAc=3/1 to 1/3) to obtain HJC-1-73 (18 mg, 36%) as a colorless oil and some recovered HJC-1-5 (30 mg). $^1$H NMR (600 MHz, CDCl$_3$) δ 7.55 (d, 2H, J=8.4 Hz), 7.51 (d, 2H, J=7.8 Hz), 7.29 (d, 2H, J=6.6 Hz), 7.28 (d, 2H, J=6.6 Hz), 3.94-3.96 (m, 1H), 3.57 (t, 2H, J=7.2 Hz), 3.36-3.41 (m, 1H), 3.29 (t, 2H, J=7.2 Hz), 3.23-3.28 (m, 1H), 3.06-3.08 (m, 1H), 3.01-3.03 (m, 1H), 2.88-2.90 (m, 2H), 2.36 (t, 2H, J=8.4 Hz), 1.94-1.99 (m, 2H), 1.33 (d, 3H, J=7.2 Hz), 1.31 (d, 3H, J=7.2 Hz), 1.27 (d, 3H, J=7.2 Hz). $^{13}$C NMR (150 MHz, CDCl$_3$) δ 175.1, 142.1, 139.8, 138.9, 138.1, 129.3, 127.8, 127.6, 127.2, 53.6, 50.5, 47.8, 44.1, 40.6, 33.6, 31.2, 19.2, 18.2, 16.8, 16.6.

Example 14

Propane-2-sulfonic acid {2-[4-(5-nitro-indol-1-yl)-phenyl]propyl}amide (HJC-1-79)

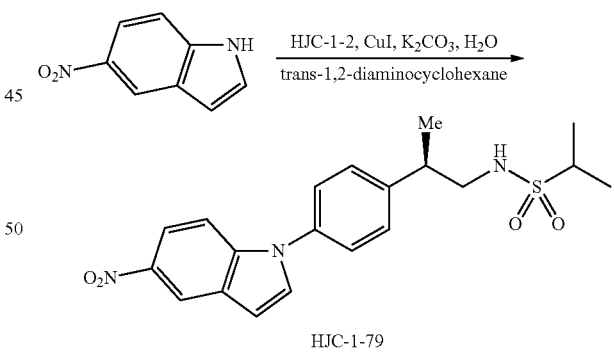

To a solution of HJC-1-2 (100 mg, 0.27 mmol) and 5-nitro-1H-indole (46 mg, 0.29 mmol) in H$_2$O (5 mL) was added K$_2$CO$_3$ (75 mg, 0.54 mmol), trans-1,2-diaminocyclohexane (3 mg, 0.027 mmol) and then CuI (3 mg, 0.014 mmol). The resulting mixture was deoxygenated via five vacuum/N$_2$-refill cycles. The mixture was stirred at 80° C. for 36 h. The mixture was partitioned between EtOAc (50 mL) and H$_2$O (10 mL). The organic layer was separated and washed with brine (10 mL), dried over anhydrous Na$_2$SO$_4$, filtered and concentrated to give an oil residue. This residue was purified with silica gel column (Hexane/EtOAc=2/1) to obtain HJC-1-79 (30 mg, 28%) as a yellow oil. $^1$H NMR (600 MHz, CDCl$_3$) δ 8.62-8.64 (m, 1H), 8.09-8.11 (m, 1H), 7.40-7.50 (m, 6H), 6.83-6.86 (m, 1H), 4.09-4.13 (m, 1H), 3.32-3.40 (m, 2H), 3.09-3.13 (m, 2H), 1.20-1.34 (m, 9H). $^{13}$C NMR (150 MHz, CDCl$_3$) δ 143.1, 142.4, 138.8, 137.6, 131.4, 129.0, 128.6, 125.2, 118.4, 118.1, 110.6, 105.8, 53.8, 50.4, 40.8, 19.2, 16.8, 16.6.

Example 15

Propane-2-sulfonic acid {2-[4-(5-amino-indol-1-yl)-phenyl]-propyl}amide (HJC-1-86)

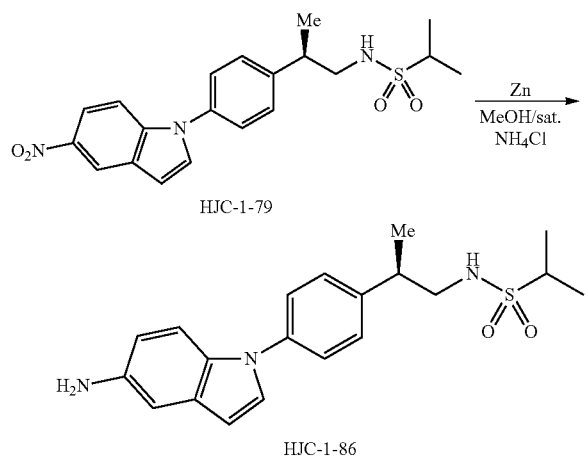

To a solution of HJC-1-79 (120 mg, 0.3 mmol) in 4 mL of MeOH was added 4 mL of saturated NH$_4$Cl (aq.). Zinc dust (195 mg, 3.0 mmol) was added into the solution at 0° C. The reaction was stirred at 0° C. for 0.5 h. TLC indicated that the starting material was gone. The mixture was partitioned between EtOAc (50 mL) and H$_2$O (10 mL). The organic layer was separated and washed with brine (10 mL), dried over anhydrous Na$_2$SO$_4$, filtered and concentrated to give an oil residue. This residue was purified with silica gel column (Hexane/EtOAc=1/1) to obtain HJC-1-86 (70 mg, 63%) as a pale brown oil. $^1$H NMR (600 MHz, CDCl$_3$) δ 7.43 (d, 2H, J=8.4 Hz), 7.37 (d, 1H, J=8.4 Hz), 7.32 (d, 2H, J=8.4 Hz), 7.24 (d, 1H, J=8.4 Hz), 6.96 (s, 1H), 6.68 (d, 1H, J=8.4 Hz), 6.49 (s, 1H), 4.29 (t, 1H, J=6.6 Hz), 3.34-3.40 (m, 2H), 3.25-3.30 (m, 2H), 3.06-3.10 (m, 1H), 3.00-3.05 (m, 1H), 1.35 (d, 3H, J=6.6 Hz), 1.32 (d, 3H, J=6.6 Hz), 1.28 (t, 3H, J=6.6 Hz). $^{13}$C NMR (150 MHz, CDCl$_3$) δ 141.1, 140.2, 139.0, 130.8, 130.5, 128.5, 128.2, 124.2, 113.2, 111.2, 106.0, 102.7, 53.6, 50.5, 40.5, 19.2, 16.9, 16.6.

Example 16

1H-indazol-5-yl)-piperidin-1-yl-methanone (HJC-1-80

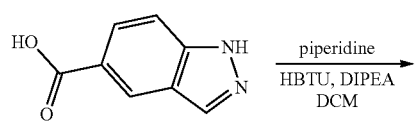

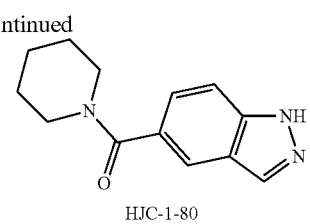

To a solution of 1H-Indazole-5-carboxylic acid (200 mg, 1.2 mmol) in 10 mL of DCM was added DIPEA (797 mg, 6.2 mmol) and piperidine (1.05 g, 12.0 mmol). HBTU (702 mg, 1.9 mmol) was added at 0° C. The resulting mixture was stirred at r.t. for 18 h. TLC indicated that the starting material was gone. The mixture was diluted with DCM (100 mL) and washed with water (30 mL). The organic layer was separated and dried over anhydrous Na$_2$SO$_4$. The solution was concentrated to give a crude product. This residue was purified with silica gel column (DCM/MeOH=50/1) to obtain HJC-1-80 (200 mg, 71%) as a yellow oil. $^1$H NMR (600 MHz, CDCl$_3$) δ 11.0 (bs, 1H), 8.10 (s, 1H), 7.82 (s, 1H), 7.50 (d, 1H, J=9.0 Hz), 7.43 (d, 1H, J=9.0 Hz), 3.69-3.72 (m, 2H), 3.40-3.65 (m, 2H), 1.70-1.76 (m, 4H), 1.61-1.64 (m, 2H).

Example 17

Propane-2-sulfonic acid (2-{4-[5-(piperidine-1-carbonyl)-indazol-1-yl]-phenyl}-propyl)-amide (HJC-2-8)

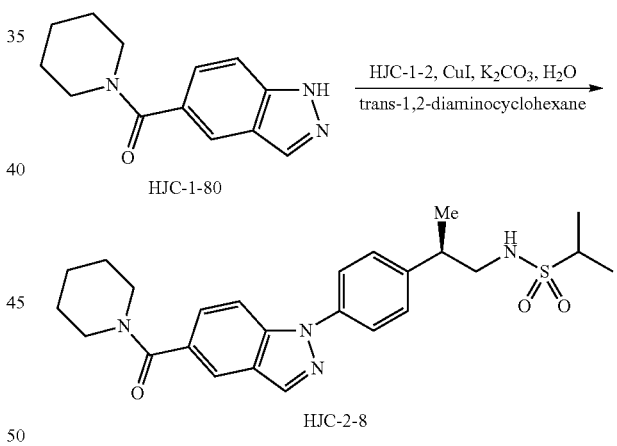

To a solution of HJC-1-2 (87 mg, 0.24 mmol) and HJC-1-80 (54 mg, 0.24 mmol) in H$_2$O (2 mL) was added K$_2$CO$_3$ (65 mg, 0.47 mmol), trans-1,2-diaminocyclohexane (3 mg, 0.02 mmol) and then CuI (2 mg, 0.01 mmol). The resulting mixture was deoxygenated via five vacuum/N$_2$-refill cycles. The mixture was stirred at 82° C. for 16 h. The mixture was partitioned between EtOAc (50 mL) and H$_2$O (10 mL). The organic layer was separated and washed with brine (10 mL), dried over anhydrous Na$_2$SO$_4$, filtered and concentrated to give an oil residue. This residue was purified with silica gel column (Hexane/EtOAc=1/1 to 1/2) to obtain HJC-2-8 (11 mg, 10%) as a pale yellow oil and the recovered HJC-1-2 (72 mg). $^1$H NMR (600 MHz, CDCl$_3$) δ 8.26 (s, 1H), 7.91 (s, 1H), 7.77 (d, 1H, J=7.8 Hz), 7.73 (d, 2H, J=6.6 Hz), 7.53 (d, 1H, J=9.0 Hz), 7.44 (d, 2H, J=7.2 Hz), 4.00-4.03 (m, 1H), 3.68-3.80 (m, 2H), 3.40-3.45 (m, 2H), 3.29-3.33 (m, 1H), 3.09-

3.15 (m, 2H), 1.55-1.74 (m, 6H), 1.39 (d, 3H, J=6.6 Hz), 1.36 (d, 4H, J=6.6 Hz), 1.33 (d, 4H, J=6.6 Hz). $^{13}$C NMR (150 MHz, CDCl$_3$) δ 170.4, 142.2, 139.0, 138.9, 136.1, 130.1, 128.6, 126.7, 124.9, 123.4, 120.7, 110.6, 53.7, 50.5, 40.8, 29.8, 24.8, 19.2, 16.8, 16.7.

Example 18

1H-Indol-5-yl)-pyrrolidin-1-yl-methanone (HJC-2-5

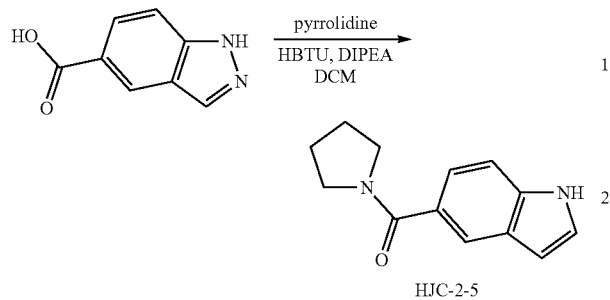

To a solution of 1H-Indole-5-carboxylic acid (161 mg, 1.0 mmol) in 10 mL of DCM was added DIPEA (646 mg, 5.0 mmol) and pyrrolidine (711 mg, 10.0 mmol). HBTU (569 mg, 1.5 mmol) was added at 0° C. The resulting mixture was stirred at r.t. for 18 h. TLC indicated that the starting material was gone. The mixture was diluted with DCM (50 mL) and washed with water (10 mL). The organic layer was separated and dried over anhydrous Na$_2$SO$_4$. The solution was concentrated to give a crude product. This residue was purified with silica gel column (Hexane/EtOAc=1/1) to obtain HJC-2-5 (180 mg, 84%) as a pale yellow solid. $^1$H NMR (600 MHz, CDCl$_3$) δ 8.44 (s, 1H), 7.86 (s, 1H), 7.38-7.42 (m, 2H), 7.27 (d, 1H, J=7.8 Hz), 6.59 (s, 1H), 3.68-3.70 (m, 2H), 3.53-3.55 (s, 2H), 1.96-1.99 (m, 2H), 1.86-1.89 (m, 2H).

Example 19

Propane-2-sulfonic acid (2-{4-[5-(pyrrolidine-1-carbonyl)-indol-1-yl]-phenyl}-propyl)amide (HJC-2-10)

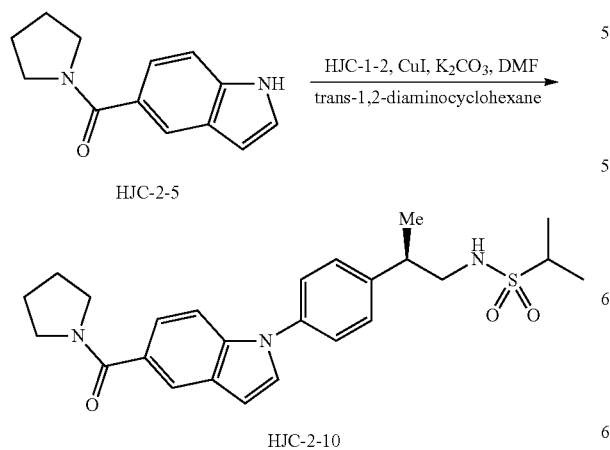

To a solution of HJC-1-2 (184 mg, 0.5 mmol) and HJC-2-5 (150 mg, 0.7 mmol) in DMF (5 mL) was added K$_2$CO$_3$ (138 mg, 1.0 mmol), trans-1,2-diaminocyclohexane (11 mg, 0.1 mmol) and then CuI (10 mg, 0.05 mmol). The resulting mixture was deoxygenated via five vacuum/N$_2$-refill cycles. The mixture was stirred at 115° C. for 36 h. The mixture was partitioned between EtOAc (100 mL) and H$_2$O (30 mL). The organic layer was separated and washed with brine (10 mL), dried over anhydrous Na$_2$SO$_4$, filtered and concentrated to give an oil residue. This residue was purified with silica gel column (Hexane/EtOAc=1/1 to 1/2) to obtain HJC-2-10 (60 mg, 18%) as a pale yellow oil. $^1$H NMR (600 MHz, CDCl$_3$) δ 7.88 (s, 1H), 7.53 (d, 1H, J=9.0 Hz), 7.47 (d, 2H, J=7.8 Hz), 7.73 (d, 1H, J=8.4 Hz), 7.37 (t, 3H, J=7.2 Hz), 6.71 (s, 1H), 3.97-4.00 (m, 1H), 3.63-3.70 (m, 2H), 3.50-3.60 (m, 2H), 3.38-3.42 (m, 1H), 3.27-3.32 (m, 1H), 3.06-3.12 (m, 2H), 1.95-2.00 (m, 2H), 1.85-1.89 (m, 2H), 1.37 (d, 3H, J=7.2 Hz), 1.34 (d, 3H, J=6.6 Hz), 1.31 (d, 3H, J=7.2 Hz). $^{13}$C NMR (150 MHz, CDCl$_3$) δ 170.8, 142.0, 138.4, 136.5, 129.6, 129.0, 128.7, 128.7 124.9, 122.2, 120.9, 110.3, 104.4, 53.7, 50.5, 50.2, 46.4, 40.7, 26.6, 24.7, 19.2, 16.8, 16.7.

Example 20

1H-indol-5-yl)-(4-methyl-piperazin-1-yl)methanone (HJC-1-94

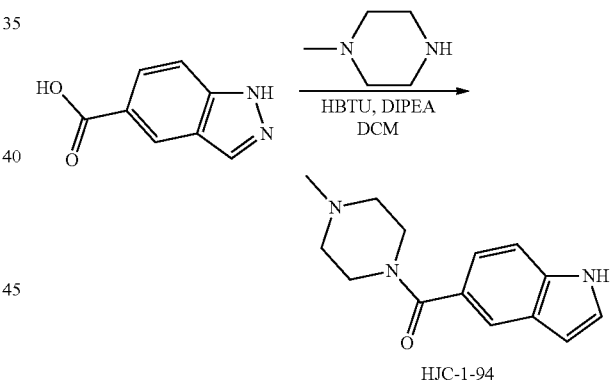

To a solution of 1H-Indole-5-carboxylic acid (323 mg, 2.0 mmol) in 10 mL of DCM was added DIPEA (1.03 g, 8.0 mmol), followed by 1-methyl-piperazine (401 mg, 4.0 mmol). HBTU (1.14 g, 3.0 mmol) was added at 0° C. The resulting mixture was stirred at r.t. for 18 h. TLC indicated that the starting material was gone. The solution was concentrated to give a crude product. The residue was diluted with EtOAc (150 mL) and washed with brine (20 mL). The organic layer was separated and dried over anhydrous Na$_2$SO$_4$. The solution was concentrated to give a crude product. This residue was purified with silica gel column (DCM/MeOH/30% NH$_3$/H$_2$O=100/10/1) to obtain HJC-1-94 (400 mg, 82%) as a brown oil. $^1$H NMR (600 MHz, CDCl$_3$) δ 8.66 (s, 1H), 7.70 (s, 1H), 7.37 (d, 1H, J=8.4 Hz), 7.23-7.26 (m, 2H), 6.57 (s, 1H), 3.62-3.78 (m, 4H), 2.44-2.49 (m, 4H), 2.04 (s, 3H).

Example 21

Propane-2-sulfonic acid 2-{4-[5-(4-methyl-piperazine-1-carbonyl)-indol-1-yl]-phenyl}-propyl)amide (HJC-2-22)

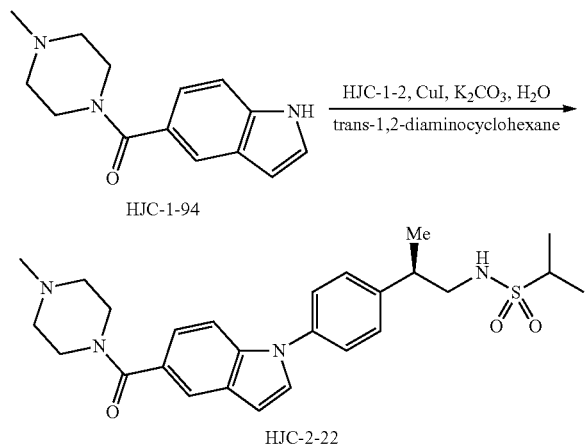

To a solution of HJC-1-2 (170 mg, 0.55 mmol) and HJC-1-94 (132 mg, 0.55 mmol) in H$_2$O (5 mL) was added K$_2$CO$_3$ (150 mg, 1.09 mmol), trans-1,2-diaminocyclohexane (12 mg, 0.11 mmol) and then CuI (10 mg, 0.055 mmol). The resulting mixture was deoxygenated via five vacuum/N$_2$-refill cycles. The mixture was stirred at 85° C. for 48 h. The mixture was partitioned between EtOAc (100 mL) and H$_2$O (30 mL). The organic layer was separated and washed with brine (10 mL), dried over anhydrous Na$_2$SO$_4$, filtered and concentrated to give an oil residue. This residue was purified with silica gel column (DCM/MeOH/30% NH$_3$/H$_2$O=100/10/1) to obtain HJC-2-22 (14 mg, 5%) as a pale yellow oil. $^1$H NMR (600 MHz, CDCl$_3$) δ 7.79 (s, 1H), 7.56 (d, 1H, J=8.4 Hz), 7.49 (d, 2H, J=7.2 Hz), 7.40 (d, 3H, J=9.0 Hz), 7.32 (d, 1H, J=7.2 Hz), 6.74 (s, 1H), 4.02-4.10 (m, 1H), 3.62-3.71 (m, 4H), 340-3.44 (m, 1H), 3.30-3.34 (m, 1H), 3.08-3.14 (m, 2H), 2.41-2.47 (m, 4H), 2.35 (s, 3H), 1.39 (d, 3H, J=6.6 Hz), 1.36 (d, 3H, J=7.2 Hz), 1.33 (d, 3H, J=7.2 Hz). $^{13}$C NMR (150 MHz, CDCl$_3$) δ 171.6, 142.1, 138.4, 136.5, 129.2, 128.9, 128.8, 128.0, 124.9, 122.0, 120.8, 110.6, 104.3, 53.7, 50.5, 46.2, 40.7, 19.2, 16.8, 16.7.

Example 22

Propane-2-sulfonic acid [2-(4-pyrrolo[2,3-b]pyridin-1-yl-phenyl)-propyl]amide (HJC-2-28)

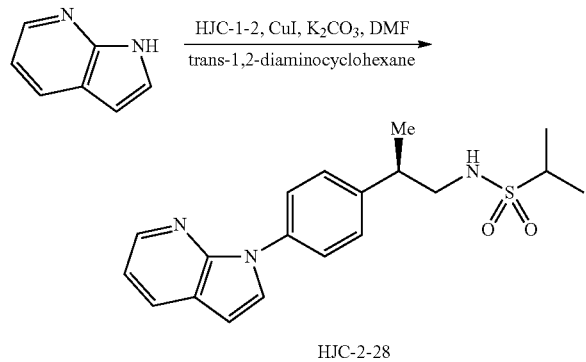

To a solution of HJC-1-2 (184 mg, 0.5 mmol) and 7-azaindole (59 mg, 0.5 mmol) in DMF (5 mL) was added K$_2$CO$_3$ (138 mg, 1.0 mmol), trans-1,2-diaminocyclohexane (11 mg, 0.1 mmol) and then CuI (10 mg, 0.05 mmol). The resulting mixture was deoxygenated via five vacuum/N$_2$-refill cycles. The mixture was stirred at 115° C. for 16 h. The mixture was partitioned between EtOAc (100 mL) and H$_2$O (30 mL). The organic layer was separated and washed with brine (10 mL), dried over anhydrous Na$_2$SO$_4$, filtered and concentrated to give an oil residue. This residue was purified with silica gel column (Hexane/EtOAc=3/1) to obtain HJC-2-28 (140 mg, 78%) as a colorless oil. $^1$H NMR (600 MHz, CDCl$_3$) δ 8.35 (d, 1H, J=4.8 Hz), 7.96 (d, 1H, J=7.8 Hz), 7.71 (d, 2H, J=8.4 Hz), 7.48 (d, 1H, J=3.0 Hz), 7.37 (d, 2H, J=7.8 Hz), 7.11-7.14 (m, 1H), 6.62 (d, 1H, J=3.6 Hz), 4.23-4.25 (m, 1H), 3.34-3.38 (m, 1H), 3.23-3.27 (m, 1H), 3.07-3.11 (m, 1H), 3.01-3.05 (m, 1H), 1.23-1.35 (m, 9H). $^{13}$C NMR (150 MHz, CDCl$_3$) δ 147.5, 143.7, 141.3, 137.4, 129.2, 128.3, 127.9, 124.5, 121.6, 116.8, 101.8, 53.6, 50.4, 40.7, 19.1, 16.8, 16.7.

Example 23

Propane-2-sulfonic acid [2-(4-pyrrolo[3,2-b]pyridin-1-yl-phenyl)-propyl]amide (HJC-2-29)

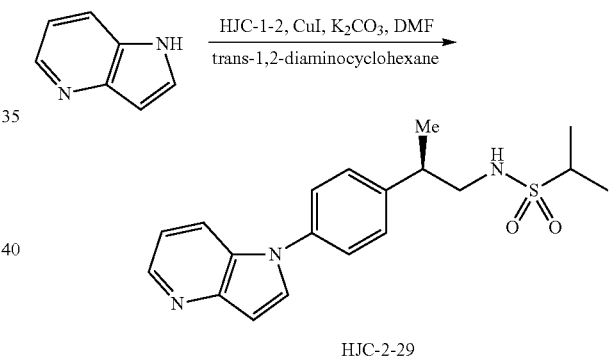

To a solution of HJC-1-2 (184 mg, 0.5 mmol) and 4-azaindole (59 mg, 0.5 mmol) in DMF (5 mL) was added K$_2$CO$_3$ (138 mg, 1.0 mmol), trans-1,2-diaminocyclohexane (11 mg, 0.1 mmol) and then CuI (10 mg, 0.01 mmol). The resulting mixture was deoxygenated via five vacuum/N$_2$-refill cycles. The mixture was stirred at 115° C. for 18 h, and was then partitioned between EtOAc (100 mL) and H$_2$O (30 mL). The organic layer was separated and washed with brine (10 mL), dried over anhydrous Na$_2$SO$_4$, filtered and concentrated to give an oil residue. This residue was purified with silica gel column (Hexane/EtOAc=1/1) to obtain HJC-2-29 (30 mg, 40%) as a pale yellow oil and the recovered 4-azaindole (34 mg). $^1$H NMR (600 MHz, CDCl$_3$) δ 8.49 (s, 1H), 7.80 (d, 1H, J=9.0 Hz), 7.54 (s, 1H), 7.41 (d, 2H, J=7.8 Hz), 7.38 (d, 2H, J=7.2 Hz), 7.12-7.14 (m, 1H), 6.87 (s, 1H), 4.37 (t, 1H, J=6.0 Hz), 3.37-3.42 (m, 1H), 3.28-3.32 (m, 1H), 3.06-3.13 (m, 2H), 1.30-1.37 (m, 9H). $^{13}$C NMR (150 MHz, CDCl$_3$) δ 147.6, 144.1, 144.1, 142.3, 137.9, 131.0, 128.9, 124.5, 117.8, 117.2, 104.7, 53.7, 50.5, 40.7, 19.2, 16.8, 16.7.

Example 24

Propane-2-sulfonic acid [2-(4-pyrrolo[3,2-c]pyridin-1-yl-phenyl)-propyl]amide (HJC-2-31)

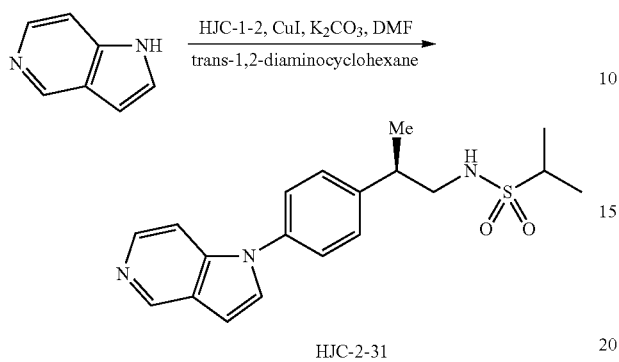

HJC-2-31

To a solution of HJC-1-2 (184 mg, 0.5 mmol) and 5-azaindole (59 mg, 0.5 mmol) in DMF (5 mL) was added K₂CO₃ (138 mg, 1.0 mmol), trans-1,2-diaminocyclohexane (11 mg, 0.1 mmol) and then CuI (10 mg, 0.05 mmol). The resulting mixture was deoxygenated via five vacuum/N₂-refill cycles. The mixture was stirred at 115° C. for 18 h, was then partitioned between EtOAc (100 mL) and H₂O (30 mL). The organic layer was separated and washed with brine (10 mL), dried over anhydrous Na₂SO₄, filtered and concentrated to give an oil residue. This residue was purified with silica gel column (Hexane/EtOAc=1/1 to 1/3) to obtain HJC-2-31 (120 mg, 67%) as a pale yellow oil. $^1$H NMR (600 MHz, CDCl₃) δ 8.93 (s, 1H), 8.22 (d, 1H, J=5.4 Hz), 7.38 (t, 4H, J=8.4 Hz), 7.35 (d, 1H, J=7.8 Hz), 7.31 (d, 1H, J=2.4 Hz), 6.74 (d, 1H, J=2.4 Hz), 5.10-5.14 (m, 1H), 3.39 (t, 1H, J=7.2 Hz), 3.31 (t, 1H, J=7.2 Hz), 3.07-3.12 (m, 2H), 1.23-1.36 (m, 9H). $^{13}$C NMR (150 MHz, CDCl₃) δ 144.2, 142.8, 141.4, 139.4, 137.4, 129.1, 128.9, 126.0, 124.5, 105.8, 103.1, 53.6, 50.4, 40.8, 19.2, 16.8, 16.7.

Example 25

Propane-2-sulfonic acid [2-(4-pyrrolo[2,3-c]pyridin-1-yl-phenyl)-propyl]amide (HJC-2-32)

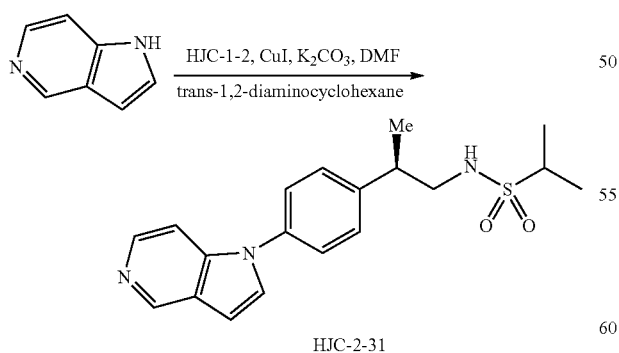

HJC-2-31

To a solution of HJC-1-2 (184 mg, 0.5 mmol) and 6-azaindole (59 mg, 0.5 mmol) in DMF (5 mL) was added K₂CO₃ (138 mg, 1.0 mmol), trans-1,2-diaminocyclohexane (11 mg, 0.1 mmol) and then CuI (10 mg, 0.05 mmol). The resulting mixture was deoxygenated via five vacuum/N₂-refill cycles. The mixture was stirred at 115° C. for 18 h, and was then partitioned between EtOAc (100 mL) and H₂O (30 mL). The organic layer was separated and washed with brine (10 mL), dried over anhydrous Na₂SO₄, filtered and concentrated to give an oil residue. This residue was purified with silica gel column (DCM/MeOH=10/1) to obtain HJC-2-32 (130 mg, 73%) as a pale yellow oil. $^1$H NMR (600 MHz, CDCl₃) δ 8.87 (s, 1H), 8.29 (d, 1H, J=6.0 Hz), 7.57 (t, 1H, J=2.4 Hz), 7.38-7.44 (m, 5H), 6.67 (d, 1H, J=3.0 Hz), 4.63 (t, 1H, J=6.0 Hz), 3.37-3.41 (m, 1H), 3.28-3.33 (m, 1H), 306-3.12 (m, 2H), 1.22-1.37 (m, 9H). $^{13}$C NMR (150 MHz, CDCl₃) δ 142.7, 139.4, 137.6, 134.3, 133.8, 133.0, 131.4, 128.9, 124.6, 115.6, 103.0, 53.6, 50.4, 40.7, 19.2, 16.8, 16.7.

Example 26

4-(1H-Indole-5-carbonyl)-piperazine-1-carboxylic acid tert-butyl ester (HJC-2-13)

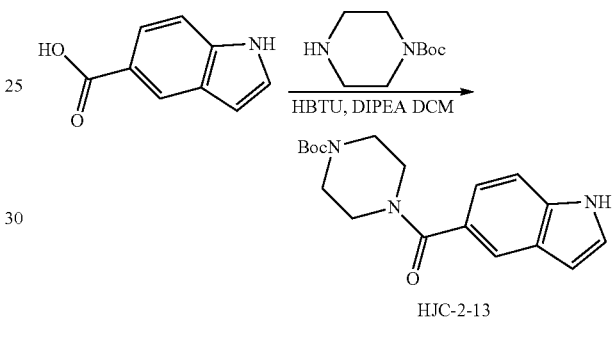

HJC-2-13

To a solution of 1H-indole-5-carboxylic acid (323 mg, 2.0 mmol) in 10 mL of DCM was added DIPEA (1.03 g, 8.0 mmol) and piperazine-1-carboxylic acid tert-butyl ester (400 mg, 2.1 mmol). HBTU (1.14 g, 3.0 mmol) was added at 0° C. The resulting mixture was stirred at r.t. for 18 h. TLC indicated that the starting material was gone. The mixture was diluted with DCM (100 mL) and washed with water (30 mL). The organic layer was separated and dried over anhydrous Na₂SO₄. The solution was concentrated to give a crude product, which was then purified with silica gel column (Hexane/EtOAc=1/1) to give HJC-2-13 (605 mg, 92%) as a yellow oil. $^1$H NMR (600 MHz, CDCl₃) δ 8.44 (s, 1H), 7.73 (s, 1H), 7.40 (d, 1H, J=8.4 Hz), 7.26-7.27 (m, 2H), 6.59 (s, 1H), 3.56-3.63 (m, 4H), 3.42-3.47 (m, 4H), 1.47 (s, 9H).

Example 27

4-(1-{4-[1-methyl-2-(propane-2-sulfonylamino)-ethyl]-phenyl}-1H-indole-5-carbonyl)-piperazine-1-carboxylic acid tert-butyl ester (HJC-2-34)

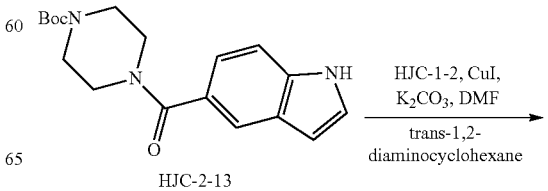

HJC-2-13

-continued

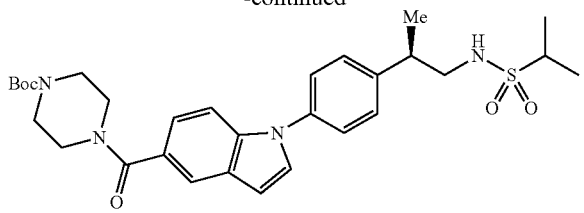

HJC-2-34

To a solution of HJC-1-2 (184 mg, 0.5 mmol) and HJC-2-13 (165 mg, 0.5 mmol) in DMF (5 mL) was added $K_2CO_3$ (138 mg, 1.0 mmol), trans-1,2-diaminocyclohexane (11 mg, 0.1 mmol) and then CuI (10 mg, 0.05 mmol). The resulting mixture was deoxygenated via five vacuum/$N_2$-refill cycles. The mixture was stirred at 115° C. for 24 h, and was then partitioned between EtOAc (100 mL) and $H_2O$ (30 mL). The organic layer was separated and washed with brine (10 mL), dried over anhydrous $Na_2SO_4$, filtered and concentrated to give an oil residue. This residue was purified with silica gel column (Hexane/EtOAc=1/1) to obtain HJC-2-34 (220 mg, 77%) as a pale yellow oil. $^1$H NMR (600 MHz, CDCl$_3$) δ 7.74 (s, 1H), 7.51 (d, 1H, J=7.8 Hz), 7.41 (d, 2H, J=7.2 Hz), 7.34 (d, 2H, J=7.2 Hz), 7.34 (s, 1H), 7.25 (d, 1H, J=8.4 Hz), 6.68 (s, 1H), 4.36-4.38 (m, 1H), 3.52-3.69 (m, 4H), 3.36-3.51 (m, 4H), 3.31-3.35 (m, 1H), 3.24-3.28 (m, 1H), 3.01-3.07 (m, 2H), 1.44 (s, 9H), 1.32 (d, 3H, J=6.6 Hz), 1.30 (d, 3H, J=6.6 Hz), 1.26 (d, 3H, J=6.6 Hz).

Example 28

Propane-2-sulfonic acid (2-{4-[5-(piperazine-1-carbonyl)-indol-1-yl]-phenyl}-propyl)amide (HJC-2-37)

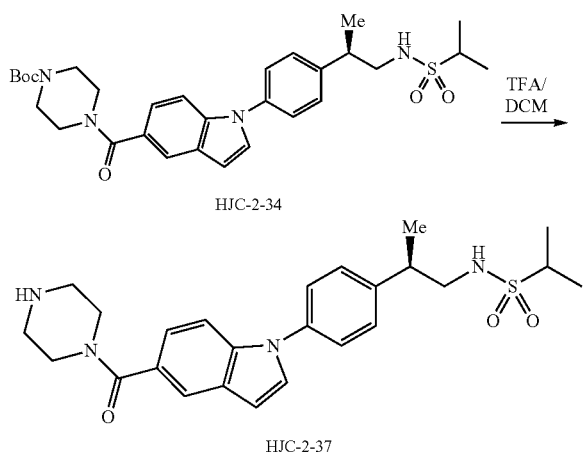

To a solution of HJC-2-34 (75 mg, 0.13 mmol) in DCM (4 mL) was added TFA (1 mL) at 0° C. The mixture was stirred at r.t. for 2 h. The reaction mixture was concentrated, and the residue was partitioned between EtOAc (50 mL) and 1 N NaHCO$_3$ (10 mL). The organic layer was washed with brine (10 mL), dried over anhydrous $Na_2SO_4$, and concentrated to give the crude product. This residue was purified with silica gel column (DCM/MeOH=15/1) to provide HJC-2-37 (50 mg, 81%) as a pale yellow oil. $^1$H NMR (600 MHz, CDCl$_3$) δ 7.76 (s, 1H), 7.53 (d, 1H, J=8.4 Hz), 7.45 (d, 2H, J=6.6 Hz), 7.37 (d, 3H, J=7.2 Hz), 7.28 (t, 2H, J=8.4 Hz), 6.71 (s, 1H), 4.27-4.30 (m, 1H), 3.53-3.63 (m, 4H), 3.38 (t, 1H, J=8.4 Hz), 3.27-3.29 (m, 1H), 3.04-3.12 (m, 2H), 2.80-2.90 (m, 4H), 1.30-1.36 (m, 9H). $^{13}$C NMR (150 MHz, CDCl$_3$) δ 171.7, 142.1, 138.3, 136.4, 129.2, 128.9, 128.7, 128.0, 124.9, 121.9, 120.7, 110.5, 104.3, 53.6, 50.4, 46.4, 46.3, 40.7, 19.2, 16.8, 16.7.

Example 29

Propane-2-sulfonic acid {2-[4-(5-cyano-indol-1-yl)-phenyl]-propyl}amide (HJC-2-35)

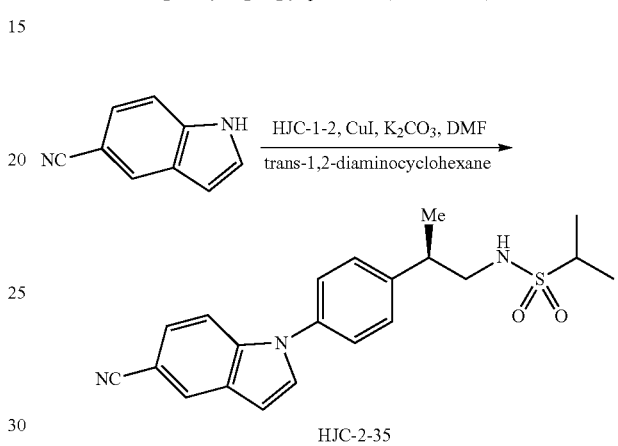

HJC-2-35

To a solution of HJC-1-2 (184 mg, 0.5 mmol) and 1H-indole-5-carbonitrile (71 mg, 0.5 mmol) in DMF (5 mL) was added $K_2CO_3$ (138 mg, 1.0 mmol), trans-1,2-diaminocyclohexane (11 mg, 0.1 mmol) and then CuI (10 mg, 0.05 mmol). The resulting mixture was deoxygenated via five vacuum/$N_2$-refill cycles. The mixture was stirred at 115° C. for 18 h. The mixture was partitioned between EtOAc (100 mL) and $H_2O$ (30 mL). The organic layer was separated and washed with brine (10 mL), dried over anhydrous $Na_2SO_4$, filtered and concentrated to give an oil residue. This residue was purified with silica gel column (Hexane/EtOAc=1/1) to obtain HJC-2-35 (110 mg, 58%) as a pale yellow oil. $^1$H NMR (600 MHz, CDCl$_3$) δ 8.00 (s, 1H), 7.26-7.56 (m, 7H), 6.73 (s, 1H), 4.37-4.42 (m, 1H), 3.36-3.40 (m, 1H), 3.29-3.33 (m, 1H), 3.06-3.13 (m, 2H), 1.28-1.40 (m, 9H). $^{13}$C NMR (150 MHz, CDCl$_3$) δ 142.9, 137.5, 130.4, 129.0, 128.9, 126.7, 125.3, 125.0, 120.6, 111.4, 104.2, 103.4, 53.6, 50.3, 40.7, 19.1, 16.7, 16.6.

Example 30

Propane-2-sulfonic acid [2-(4-indol-1-yl-phenyl)-propyl]amide (HJC-2-46)

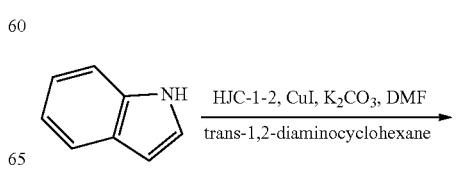

-continued

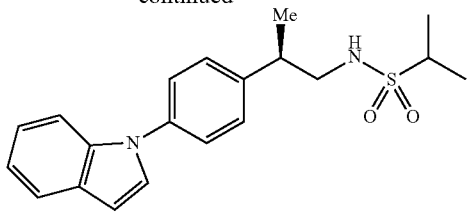

HJC-2-46

To a solution of HJC-1-2 (147 mg, 0.4 mmol) and indole (47 mg, 0.4 mmol) in DMF (5 mL) was added $K_2CO_3$ (111 mg, 0.8 mmol), trans-1,2-diaminocyclohexane (9 mg, 0.08 mmol) and then CuI (8 mg, 0.04 mmol). The resulting mixture was deoxygenated via five vacuum/$N_2$-refill cycles. The mixture was stirred at 115° C. for 24 h, and was then partitioned between EtOAc (100 mL) and $H_2O$ (30 mL). The organic layer was separated and washed with brine (10 mL), dried over anhydrous $Na_2SO_4$, filtered and concentrated to give an oil residue. This residue was purified with silica gel column (Hexane/EtOAc=3/1 to 1/1) to obtain HJC-2-46 (50 mg, 35%) as a pale yellow oil. $^1$H NMR (600 MHz, $CDCl_3$) δ 7.70 (d, 1H, J=7.8 Hz), 7.60 (d, 1H, J=8.4 Hz), 7.49 (d, 2H, J=7.8 Hz), 7.37 (d, 2H, J=7.8 Hz), 7.33 (d, 1H, J=3.0 Hz), 7.24-7.26 (m, 1H), 7.18 (t, 1H, J=7.8 Hz), 6.70 (s, 1H), 4.07-4.10 (m, 1H), 3.38-3.42 (m, 1H), 3.28-3.32 (m, 1H), 3.04-3.12 (m, 2H), 1.26-1.38 (m, 9H). $^{13}$C NMR (150 MHz, $CDCl_3$) δ 141.5, 138.8, 135.9, 129.4, 128.6, 128.0, 124.8, 122.5, 121.3, 120.5, 110.6, 103.8, 53.6, 50.5, 40.6, 19.2, 16.8, 16.7.

Example 31

Pyridine-2-carboxylic acid (1-{4-[1-methyl-2-(propane-2-sulfonylamino)-ethyl]-phenyl}-1H-indol-5-yl)amide (HJC-2-48)

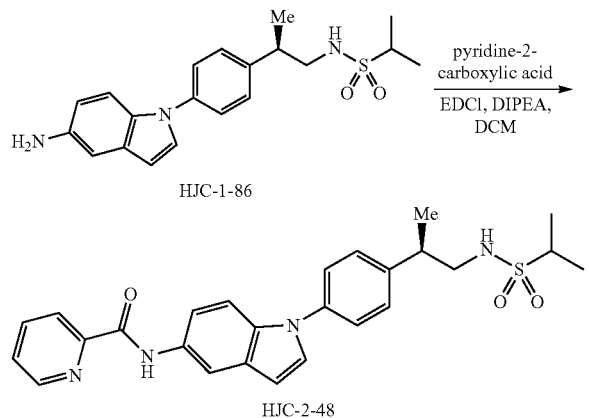

To a solution of HJC-1-86 (25 mg, 0.067 mmol) and pyridine-2-carboxylic acid (10 mg, 0.074 mmol) in 2 mL of DCM was added DIPEA (17 mg, 0.13 mmol). EDCI (14 mg, 0.087 mmol) was added at 0° C. The resulting mixture was stirred at r.t. for 48 h. The solution was diluted with DCM (50 mL), washed with 1 N HCl (aq.) (2 mL) and brine (10 mL). The organic layer was dried over anhydrous $Na_2SO_4$, and then concentrated under reduced pressure. The residue was purified by silica gel column chromatography (Hexane/EtOAc=3/1 to 1/1) to give the desired product as a colorless oil (27 mg, 82%). $^1$H NMR (600 MHz, $CDCl_3$) δ 10.07 (s, 1H), 8.63 (d, 1H, J=4.8 Hz), 8.33 (d, 1H, J=7.8 Hz), 8.25 (s, 1H), 7.91 (t, 1H, J=7.2 Hz), 7.47-7.55 (m, 5H), 7.36 (d, 2H, J=7.8 Hz), 7.33 (s, 1H), 6.68 (s, 1H), 4.06-4.09 (m, 1H), 3.38-3.42 (m, 1H), 3.27-3.31 (m, 1H), 3.04-3.11 (m, 2H), 1.36 (d, 3H, J=6.6 Hz), 1.33 (d, 3H, J=6.6 Hz), 1.30 (d, 3H, J=7.2 Hz). $^{13}$C NMR (150 MHz, $CDCl_3$) δ 161.9, 150.3, 148.0, 141.5, 138.7, 137.8, 133.2, 131.2, 129.7, 128.8, 128.7, 126.3, 124.6, 122.5, 116.1, 112.4, 110.9, 104.0, 53.7, 50.5, 40.7, 19.2, 16.8, 16.7.

Example 32

Propane-2-sulfonic acid (2-{4-[5-(4-methanesulfonyl-piperazine-1-carbonyl)-indol-1-yl]-phenyl}-propyl)amide (HJC-2-67)

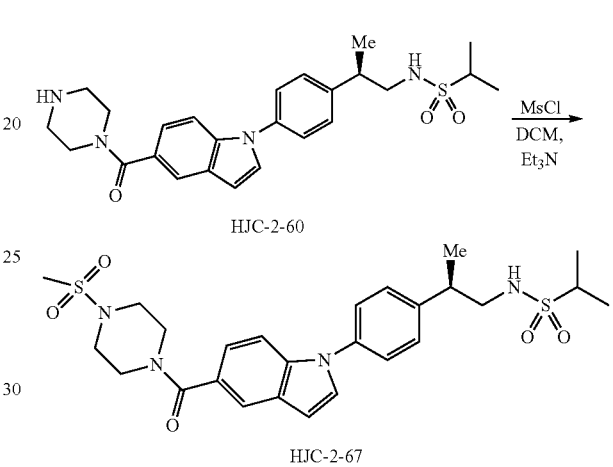

To a solution of HJC-2-60 (30 mg, 0.064 mmol) and $Et_3N$ (13 mg, 0.13 mmol) in 3 mL of DCM was added MsCl (15 mg, 0.13 mmol) at 0° C. The resulting mixture was stirred at r.t. for 2 h. The solution was diluted with DCM (50 mL), washed with 1 N HCl (aq.) (1 mL) and brine (10 mL). The organic layer was dried over anhydrous $Na_2SO_4$, and then concentrated under reduced pressure. The residue was purified by silica gel column chromatography (Hexane/EtOAc=1/1 to 1/3) to give the desired product as a colorless oil (27 mg, 77%). $^1$H NMR (600 MHz, $CDCl_3$) δ 7.77 (s, 1H), 7.54 (d, 1H, J=8.4 Hz), 7.45 (d, 2H, J=7.8 Hz), 7.36-7.38 (m, 3H), 7.28 (d, 1H, J=8.4 Hz), 6.72 (s, 1H), 4.10-4.13 (m, 1H), 3.80-3.85 (m, 4H), 3.33-3.40 (m, 1H), 3.16-3.30 (m, 5H), 3.06-3.16 (m, 2H), 2.80 (s, 3H), 1.36 (d, 3H, J=6.6 Hz), 1.33 (d, 3H, J=7.2 Hz), 1.30 (d, 3H, J=7.2 Hz). $^{13}$C NMR (150 MHz, $CDCl_3$) δ 171.9, 142.3, 138.2, 136.7, 129.5, 128.9, 128.8, 126.9, 124.9, 121.9, 121.1, 110.8, 104.3, 53.7, 50.4, 50.4, 46.0, 40.7, 34.9, 19.2, 16.8, 16.7.

Example 33

Propane-2-SULFONIC ACID (2-{4-[5-(4-acetyl-piperazine-1-carbonyl)-indol-1-yl]-phenyl}-propyl)amide (HJC-2-68)

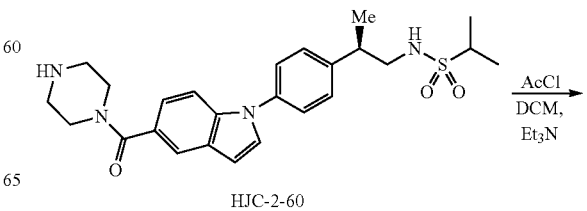

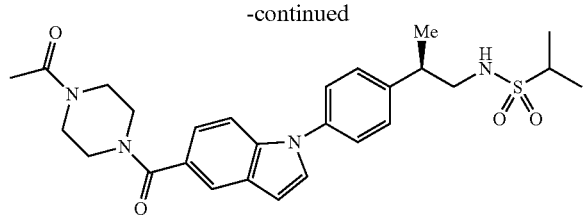

HJC-2-68

To a solution of HJC-2-60 (47 mg, 0.1 mmol) and Et₃N (20 mg, 0.2 mmol) in 3 mL of DCM was added AcCl (16 mg, 0.2 mmol at 0° C. The resulting mixture was stirred at r.t. for 2 h. The solution was diluted with DCM (50 mL), washed with 1 N HCl (aq.) (1 mL) and brine (10 mL). The organic layer was dried over anhydrous $Na_2SO_4$, and then concentrated under reduced pressure. The residue was purified by silica gel column chromatography (EtOAc) to give the desired product as a colorless oil (45 mg, 88%). $^1$H NMR (600 MHz, CDCl₃) δ 7.77 (s, 1H), 7.54 (d, 1H, J=7.8 Hz), 7.44 (d, 2H, J=7.8 Hz), 7.36-7.39 (m, 3H), 7.28 (d, 1H, J=8.4 Hz), 6.71 (s, 1H), 4.22-4.28 (m, 1H), 3.63-3.72 (m, 8H), 3.35-3.39 (m, 1H), 3.28-3.30 (m, 1H), 3.06-3.11 (m, 2H), 2.12 (s, 3H), 1.35 (d, 3H, J=6.6 Hz), 1.32 (d, 3H, J=5.4 Hz), 1.29 (d, 3H, J=5.4 Hz). $^{13}$C NMR (150 MHz, CDCl₃) δ 171.9, 169.3, 142.3, 138.2, 136.7, 129.4, 128.9, 128.8, 127.2, 124.9, 121.9, 120.9, 110.7, 104.3, 53.6, 50.4, 46.4, 41.7, 40.7, 21.5, 19.2, 16.8, 16.7.

Example 34

4-Iodo-pyridin-2-yl)-piperidin-1-yl-methanone (HJC-2-63

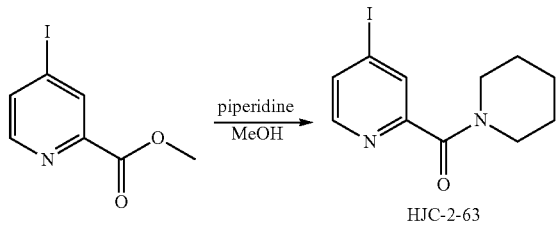

HJC-2-63

To a solution of 4-iodo-pyridine-2-carboxylic acid methyl ester (263 mg, 1.0 mmol) in 1 mL of MeOH was added 1 mL of piperidine. The resulting mixture was stirred at r.t. for 36 h. TLC indicated that the starting material was gone. The mixture was diluted with EtOAc (50 mL) and washed with water (20 mL). The organic layer was separated and washed with 0.5 N HCl (10 mL) and then brine (10 mL). After drying over anhydrous $Na_2SO_4$, the solution was concentrated to give a pale yellow oil (270 mg, 85%). $^1$H NMR (600 MHz, CDCl₃) δ 8.21 (d, 1H, J=4.8 Hz), 7.95 (s, 1H), 7.69 (d, 1H, J=3.6 Hz), 3.65-3.71 (m, 2H), 3.39-3.43 (m, 2H), 1.61-1.70 (m, 4H), 1.55-1.62 (m, 2H).

Example 35

Propane-2-sulfonic acid (2-{4-[2-(piperidine-1-carbonyl)-pyridin-4-yl]-phenyl}-propyl)-amide (HJC-2-69)

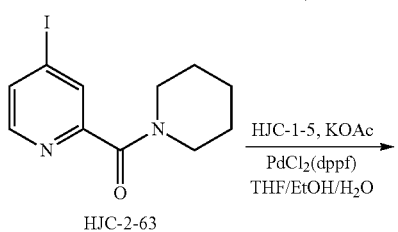

HJC-2-63

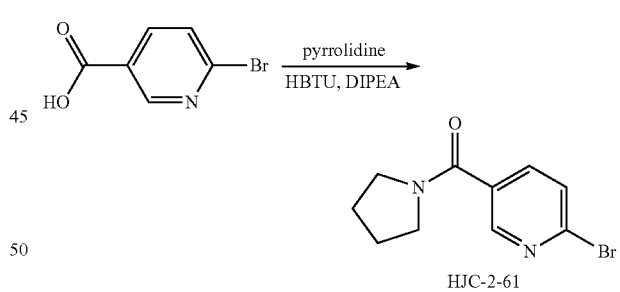

HJC-2-69

To a solution of HJC-1-5 (129 mg, 0.35 mmol) and HJC-2-63 (110 mg, 0.35 mmol) in THF/EtOH/H₂O (4 mL/4 mL/4 mL) was added KOAc (103 mg, 1.05 mmol) and then Pd(dppf)Cl₂ (28 mg, 0.035 mmol). The resulting mixture was deoxygenated via five vacuum/N₂-refill cycles. The mixture was stirred at 80° C. for 24 h, and was then concentrated under vacuum. The residue was partitioned between EtOAc (50 mL) and H₂O (20 mL). The organic layer was separated and washed with brine (10 mL), dried over anhydrous $Na_2SO_4$, filtered and concentrated to give an oil residue. This residue was purified with silica gel column (Hexane/EtOAc=1/1 to 1/3) to obtain HJC-2-69 (110 mg, 77%) as a red oil. $^1$H NMR (600 MHz, CDCl₃) δ 8.56 (d, 1H, J=4.8 Hz), 7.72 (s, 1H), 7.58 (d, 2H, J=7.2 Hz), 7.47 (d, 1H, J=4.8 Hz), 7.30 (d, 2H, J=7.2 Hz), 4.56-4.60 (m, 1H), 3.69-3.72 (m, 2H), 3.39-3.42 (m, 2H), 3.28-3.31 (m, 1H), 3.21-3.26 (m, 1H), 2.98-3.03 (m, 2H), 1.60-1.66 (m, 4H), 1.50-1.55 (m, 2H), 1.28 (d, 3H, J=6.0 Hz), 1.25 (d, 3H, J=6.6 Hz), 1.22 (d, 3H, J=6.6 Hz). $^{13}$C NMR (150 MHz, CDCl₃) δ 167.7, 155.3, 149.0, 149.0, 145.0, 136.1, 128.2, 127.4, 121.7, 120.8, 53.4, 50.2, 48.3, 43.3, 40.6, 26.5, 25.6, 24.5, 19.0, 16.6, 16.5.

Example 36

6-Bromo-pyridin-3-yl)-pyrrolidin-1-yl-methanone (HJC-2-61

To a solution of 6-bromo-nicotinic acid (404 mg, 2.0 mmol) in 15 mL of DCM was added DIPEA (1.29 g, 10.0 mmol) and pyrrolidine (711 mg, 10.0 mmol). HBTU (1.14 g, 3.0 mmol) was added at 0° C. The resulting mixture was stirred at r.t. for 18 h. TLC indicated that the starting material was gone. The mixture was diluted with DCM (100 mL) and washed with water (30 mL). The organic layer was separated and dried over anhydrous $Na_2SO_4$. The solution was concentrated to give a crude product, which was purified with silica gel column (Hexane/EtOAc=2/1) to obtain HJC-2-61 (400 mg, 78%) as a pale yellow oil. $^1$H NMR (600 MHz, CDCl₃) δ 8.54 (s, 1H), 7.73 (d, 1H, J=7.8 Hz), 7.55 (d, 1H, J=7.8 Hz), 3.64 (t, 2H, J=6.6 Hz), 3.44 (t, 2H, J=6.0 Hz), 1.96-2.00 (m, 2H), 1.92-1.96 (m, 2H).

Example 37

Propane-2-sulfonic acid (2-{4-[5-(pyrrolidine-1-carbonyl)-pyridin-2-yl]-phenyl}-propyl)-amide (HJC-2-70)

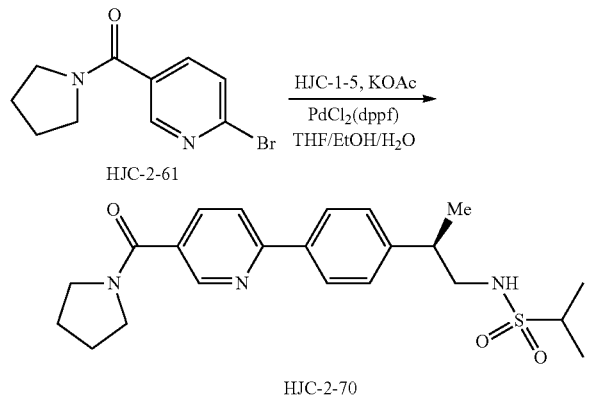

To a solution of HJC-1-5 (172 mg, 0.47 mmol) and HJC-2-61 (90 mg, 0.35 mmol) in THF/EtOH/H₂O (4 mL/4 mL/4 mL) was added KOAc (138 mg, 1.41 mmol) and then Pd(dppf)Cl₂ (38 mg, 0.047 mmol). The resulting mixture was deoxygenated via five vacuum/N₂-refill cycles. The mixture was stirred at 80° C. for 18 h, and was then concentrated under vacuum. The residue was partitioned between EtOAc (50 mL) and H₂O (20 mL). The organic layer was separated and washed with brine (10 mL), dried over anhydrous Na₂SO₄, filtered and concentrated to give an oil residue. This residue was purified with silica gel column (Hexane/EtOAc=1/1 to 1/3) to obtain HJC-2-70 (60 mg, 41%) as a pale red oil. ¹H NMR (600 MHz, CDCl₃) δ 8.83 (s, 1H), 7.96 (d, 2H, J=7.2 Hz), 7.92 (d, 1H, J=7.8 Hz), 7.74 (d, 1H, J=8.4 Hz), 7.32 (d, 2H, J=7.2 Hz), 4.15-4.21 (m, 1H), 3.66 (t, 2H, J=6.6 Hz), 3.51 (t, 2H, J=6.6 Hz), 3.36-3.38 (m, 1H), 3.23-3.27 (m, 1H), 3.00-3.06 (m, 2H), 1.97 (t, 2H, J=6.6 Hz), 1.91 (t, 3H, J=6.0 Hz), 1.31 (d, 3H, J=6.6 Hz), 1.28 (d, 3H, J=6.6 Hz), 1.24 (d, 3H, J=6.0 Hz). ¹³C NMR (150 MHz, CDCl₃) δ 167.2, 158.1, 148.3, 144.9, 137.5, 136.2, 131.1, 127.9, 127.6, 119.9, 53.5, 50.3, 49.7, 46.5, 40.8, 26.6, 24.5, 19.1, 16.7, 16.6.

Example 38

2-Fluoro-N-(1-{4-[1-methyl-2-(propane-2-sulfonylamino)-ethyl]phenyl}-1H-indol-5-yl)-propionamide (HJC-5-64)

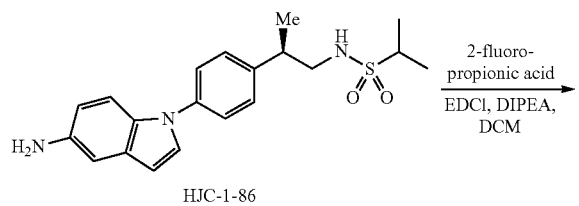

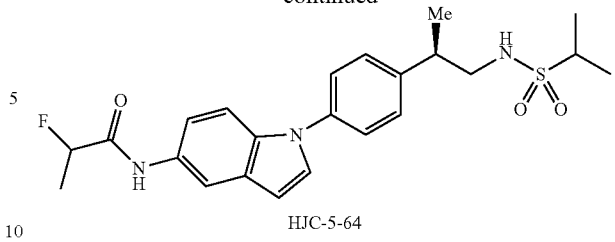

To a solution of HJC-1-86 (74 mg, 0.2 mmol) and 2-fluoro-propionic acid (28 mg, 0.3 mmol) in 5 mL of DCM was added DIPEA (77 mg, 0.6 mmol). EDCI (62 mg, 0.4 mmol) was added at 25° C. The resulting mixture was stirred at 25° C. for 12 h. The solution was diluted with DCM (20 mL), washed with H₂O (10 mL) and brine (10 mL). The organic layer was dried over anhydrous Na₂SO₄, and then concentrated under reduced pressure. The residue was purified by silica gel column chromatography (Hexane/EtOAc=1/1) to give the desired product as a pale brown oil (85 mg, 96%). ¹H NMR (600 MHz, CDCl3) δ 8.09 (d, 1H, J=6.6 Hz), 7.98 (d, 1H, J=1.8 Hz), 7.48 (d, 1H, J=8.4 Hz), 7.43 (d, 2H, J=8.4 Hz), 7.35 (d, 2H, J=8.4 Hz), 7.31 (d, 1H, J=3.6 Hz), 7.27-7.29 (m, 1H), 6.65 (d, 1H, J=3.0 Hz), 5.10-5.20 (m, 1H), 4.21-4.23 (m, 1H), 3.35-3.38 (m, 1H), 3.26-3.30 (m, 1H), 3.04-3.10 (m, 2H), 1.67-1.72 (m, 3H), 1.35 (d, 3H, J=6.6 Hz), 1.32 (d, 3H, J=6.6 Hz), 1.28 (d, 3H, J=6.6 Hz). ¹³C NMR (150 MHz, CDCl3) δ 168.7 (d, J=18.8 Hz), 141.7, 138.5, 133.5, 129.9, 129.6, 129.0, 128.6, 124.6, 116.4, 113.1, 110.8, 103.9, 89.1 (d, J=183.3 Hz), 53.6, 50.4, 40.6, 19.2, 18.7 (d, J=22.2 Hz), 16.7, 16.6.

Example 39

Propane-2-sulfonic acid [2-(4-{5-[4-(2-fluoro-propionyl)-piperazine-1-carbonyl]-indol-1-yl}-phenyl)-propyl]-amidepropionamide (HJC-5-59)

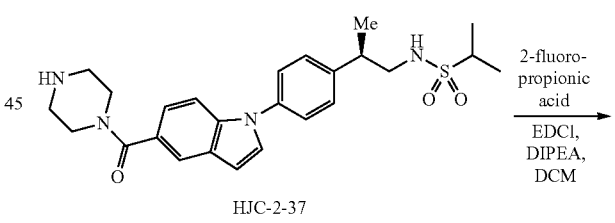

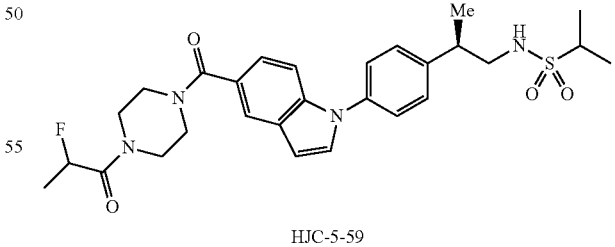

To a solution of HJC-2-37 (80 mg, 0.17 mmol) and 2-fluoro-propionic acid (24 mg, 0.26 mmol) in 5 mL of DCM was added DIPEA (66 mg, 0.51 mmol). EDCI (53 mg, 0.34 mmol) was added at 25° C. The resulting mixture was stirred at 25° C. for 12 h. The solution was diluted with DCM (20 mL), washed with H₂O (10 mL) and brine (10 mL). The organic layer was dried over anhydrous Na2SO4, and then concentrated under reduced pressure. The residue was purified by silica gel column chromatography (Hexane/EtOAc=1/1) to give the desired product as a colorless oil (80 mg, 87%). $^1$H NMR (600 MHz, CDCl3) δ 7.76 (d, 1H, J=1.2 Hz), 7.52 (d, 1H, J=8.4 Hz), 7.42 (d, 2H, J=8.4 Hz), 7.35-7.37 (m, 3H), 7.26-7.29 (m, 1H), 6.70 (d, 1H, J=3.0 Hz), 5.21-5.30 (m, 1H), 4.43-4.45 (m, 1H), 3.53-3.80 (m, 8H), 3.27-3.34 (m, 2H), 3.03-3.08 (m, 2H), 1.54-1.59 (m, 3H), 1.33 (d, 3H, J=7.2 Hz), 1.30 (d, 3H, J=7.2 Hz), 1.27 (d, 3H, J=7.2 Hz). $^{13}$C NMR (150 MHz, CDCl3) δ 171.9, 167.8 (d, J=19.2 Hz), 142.3, 138.0, 136.6, 129.4, 128.8, 128.7, 127.0, 124.8, 121.8, 120.9, 110.7, 104.2, 86.9 (d, J=178.1 Hz), 53.5, 45.5, 44.3, 42.6, 40.6, 19.1, 17.8 (d, J=21.6 Hz), 16.7, 16.6.

Example 40

Biological Assays

The ability of the invented compounds to modulate AMPA receptor (AMPAR)-mediated responses may be determined (a) by monitoring calcium influx in HEK 293 cells stably transfected with recombinant human AMPAR(s), (b) by measuring phencyclidine (PCP)-induced caspase-3 enzymatic activities in cultured organotypic cortical-striatal slices, (c) by image-analysis of cleaved caspase-3 immunoreactive neurons in developing rat brain exposed to PCP on postnatal day 7 (PND7) and, (d) by image-analysis of the density of parvalbumin-containing interneurons in cortex of young adult rat brain (PND56) exposed to PCP on postnatal day 7 (PND7), and (e) by assessing locomotor activity in young adult rats injected with PCP on PND7.

A. Calcium Influx Assay

The fluorometric imaging plate reader (FLIPR) assay was used to monitor the ability of a compound to potentiate glutamate-evoked calcium influx into HEK293 cells stably expressing human GluA1 flip (hGluA1i), GluA3 flip (hGluA3i) or hGluA1i/hGluA3i. The transfected HEK cells form functional homotetrameric or heterotetrameric AMPA receptors (AMPAR). The transfected cells were plated onto PDL (poly-D-lysine)-coated Costar 96-well clear bottom black plates at a density of $4 \times 10^4$ per well and maintained at 36° C. and in 5% $CO_2$ in ATCC complete growth medium supplemented with 10% fetal bovine serum (FBS), 1% penicillin G sodium (10,000 Units/ml)/streptomycin (10 mg/ml) and, 4 mM L-glutamine) until reaching 70-80% confluence. The medium was then discarded. The cells were washed once with HBSS+ (Hank's balanced saline solution with calcium and magnesium), and serum and antibiotics-free ATCC medium were added and cultured overnight.

After 24 hrs, when cells form a monolayer of about 90% confluence, the medium in each well was discarded, and the cells were washed with HBSS– (without calcium and magnesium) and to each well was added 80 μl of FLIPR calcium 4 component A dissolved in HBSS– containing 2.5 mM probenecid. The plate was then incubated at 36° C. and in 5% $CO_2$ in the dark for 45 min and then transferred into a Molecular Devices FLIPR FlexStation 3.

For each test of a compound of invention or reference (such as cyclothiazide, aniracetam), 8 treatments were examined: control (HBSS–), glutamate (10 μM), glutamate plus pretreatment (30 min prior to glutamate) of six (6) serial concentrations of a compound or reference. Compounds of the invention and reference were dissolved in 100% DMSO to yield 10 mM stock solutions and then further diluted to 5× of serial final concentrations as determined (up to 10 μM) with high calcium HBSS solution (10 mM HEPES, pH 7.4, 160 mM NaCl 4.5 mM KCl, 20 mM $CaCl_2$, 1 mM $MgCl_2$, 10 mM glucose). The highest final DMSO concentration in the assay was 0.1% which showed no effect on calcium influx in untreated HEK293 cells stably expressing the transfect cDNAs. Glutamate (glutamic acid) was dissolved in double distilled water (dd$H_2$O) to yield 10 mM stock solution and then diluted to 5× of its final concentration (10 μM) with high calcium HBSS solution. The prepared solutions of a compound or reference were loaded into corresponding wells of a feeding plate which were then transferred into a Molecular Devices FLIPR FlexStation 3.

Fluorometric readings were taken from each well every 1.7 seconds for 20 seconds before any addition to record baseline value and for 70 seconds after addition of any compound(s) to monitor the induced changes of calcium influx. Each well's peak fluorescence reading after addition of compound(s) represents effect of a certain concentration of a given compound(s) after subtracting the average baseline fluorescence. Peak fluorometric reading from duplicate or triplicate wells was averaged, and represents the effect of a certain concentration on calcium influx after subtracting control value. Each concentration's value was normalized to 10 μM glutamate and each compound's data points were fitted with a sigmoidal function (bottom asymptote=100, nHill=1) by using Prism from GraphPad (San Diego, Calif.) to determine the compound's $EC_{50}$ (affinity or potency). Each compound's $EC_{50}$ was summarized from at least 3 individual experiments and presented as the mean±SE.

The test of each compound includes two steps. In step one, it was tested in a single experiment in duplicate 7-point curves at final concentrations of log intervals (0, 0.0001-10 μM). Compounds showing promise, i.e. ~$EC_{50}$<10 μM and slope 0.8-1.20, were further screened in a paradigm in which each selected compound is tested in 3 independent experiments to determine its $EC_{50}$ and slope values by adding seven triplicate serial concentrations of the compound at approximately half-log intervals.

B. Measurement of Caspase-3 Enzyme Activities

Compounds showing significant AMPAR PAM effects on glutamate-induced calcium influx in HEK293 expressing hGluA1i/3i were further tested for their ability to prevent PCP-induced caspase-3 activation in our established in vitro organotypic slice model (Wang et al., *Neuropsychopharmacology* 32(5): 1178-1194, 2007). Initial screening includes two steps. In step one, all candidates were tested in a single experiment to determine an appropriate approximate concentration range for its effect on PCP-induced caspase-3 activity by adding eight serial concentrations of the compound at log intervals (0, 0.0001-10 μM). Compounds showing promising ~$IC_{50}$ (<10 μM) and slope (0.8-1.20) was further screened in a paradigm in which each selected compound was tested in 3 independent experiments to determine its $IC_{50}$ and slope values by adding eight serial concentrations of the compound at approximately half-log intervals. For all initial screening experiments, rat organotypic brain slice cultures were prepared as previously described (Wang et al., *Neuropsychopharmacology* 32(5): 1178-1194, 2007). All experiments were executed on DIV10. In each experiment, the slices were pretreated with the solution vehicle (0.1% DMSO) or 6 serial concentrations of the new compounds for 15 min, followed with (±)APMA (1 μM) (or its vehicle, 0.1% DMSO) for another 15 min. PCP (3 μM) or its vehicle (saline) was added and incubation continued for 6 hrs. The superficial cortical layers of each treated slice were harvested with the aid of an inverted microscopy and placed into ice-cold lysis buffer. Supernatants were collected and caspase-3 activity measured as described previously (Wang et al., *Neuropsychopharmacology* 32(5): 1178-1194, 2007). Caspase-3 activity was measured over 60 min and calculated as the difference between the substrate degradation rate in samples containing and those not containing Z-DEVD-FMK, a selective caspase-3 inhibitor. Data are expressed as DEVDase activity (AFC pmoles/mg protein/60 min). Protein was measured by the bicinchoninic acid (BCA) technique (Smith et al., 1985), using bovine serum albumin as standards. Each activity measurement was averaged from duplicate samples. Baseline activity (saline treated) was subtracted from all treatments. The caspase-3 activity of in slices incubated with PCP alone served as a positive control. Each compound's activity was normalized to the protective effect of (±)AMPA against PCP (100%). $IC_{50}$ and slope values were analyzed and determined with the SigmaPlot four-parameter equation as described previously (Petukhov et al., *J Med Chem* 47(12): 3009-3018, 2004). Each compound's $IC_{50}$ and slope values were determined from data in at least 3 individual experiments. Group data is reported as mean±SEM.

C. Image Analysis of Cleaved Caspase-3 Immunoreactive Neurons

PCP induces developmental neuroapoptosis via caspase-3 activation in vulnerable neurons (Wang et al., *Neuropsychopharmacology* 32(5): 1178-1194, 2007). Caspase-3 activation in vivo can be observed by immunohistochemistry with specific antibodies against cleaved caspase-3 protein and quantified by image analysis of cleaved caspase-3 immunoreactive neurons in specific brain region(s) or sub-region(s) in developing brain. Compounds showing significant AMPAR PAM effects on glutamate-induced calcium influx in HEK293 expressing hGluA1i/3i and significant preventive effect on PCP-induced caspase-3 enzyme activities in organotypic slices were further defined their abilities to block PCP-induced apoptosis in vivo.

PND7 rat pups were used in the in vivo studies. Timed pregnant Sprague-Dawley rats (Charles River Laboratories) were received on embryonic day 15 (E14, with the day after breeding considered E0) and housed individually with a 12 h light-dark cycle (lights on at 0700 hours, off at 1900 hours) in a temperature- and humidity-controlled environment with free access to food and water. Rat pups were culled on PND2 (E21 will be set up as PND0) to four of each gender to ensure an equal number of both sexes in each litter. For each compound, the test was a two step approach. Step 1 screened a dose range of a selected candidate in vivo by monitoring caspase-3 enzymatic activities in frontal cortex including motor cortex (M2/1). Step 2 performed a detailed morphometric image analysis of cleaved caspase-3 immunoreactive neurons to determining its efficacy in the superficial layers 2-4 of motor cortex (M2/1).

In step 1, each candidate was tested in two (n=2) individual experiments by using PND7 rat pups from 2 different liters. In each experiment, eight PND7 rat pups of either gender from the same liter were treated with either saline (10 ml/kg, s.c.), or PCP (10 mg/kg, s.c.), or six serial doses of a selected candidate at log intervals (0.001-100 mg/kg, i.p., 30 min prior to PCP) followed with PCP (10 mg/kg). Pups were sent back to their mother immediately after injection and its total time of absence from their mothers was limited less than 2 minutes. Six hours after PCP injection, brain tissues from M (2/1) cortex were harvested and processed to measure caspase-3 enzyme activity as described above (Wang et al., *Neuropsychopharmacology* 32(5): 1178-1194, 2007). The enzyme activity of saline-treated pup was subtracted from PCP and all other treatments. The activity percentages (%) of each dose vs. PCP were calculated to estimate its $IC_{50}$ which was used to determine its in vivo effective dose range for the step 2 study.

In step 2, each candidate was tested in four to six (n=4-6) individual experiments by using PND7 rat pups from 6 different litters. In each experiment, eight PND7 rat pups of either gender from the same litter were treated with either saline (10 ml/kg, s.c.), or PCP (10 mg/kg, s.c.), or six serial doses of a selected candidate at approximate half-log intervals log intervals (i.p., 30 min prior to PCP) followed with PCP. Nine hours later, pups were deeply anesthetized with 100 mg/kg pentobarbital sodium and their brains fixed as described previously (Wang et al., *Neuropsychopharmacology* 32(5): 1178-1194, 2007). The brain was serially cut on a Vibratome into 50 micron-thick coronal sections. According to the principles of unbiased, systematic random sampling (West, 1993), the serial sections were transferred into one of six wells, with every sixth section being placed in the same well with antifreeze solution and kept at −20° C. for further immunohistochemistry (IHC) studies. The IHC labeling of cleaved caspase-3 (Casp-3-IHC) was conducted as previously described (Wang et al., 2007). Briefly, for each animal, 3-4 free-floating sections removed from antifreeze solution were washed with PBS (0.01 M, pH 7.4), quenched for 10 min in 3% hydrogen peroxide/methanol, blocked for 1 hr with 2% normal goat serum/2% BSA/0.2% milk/0.1% Triton X-100 in PBS and incubated overnight with rabbit anti-cleaved caspase-3 (Asp175, 1:1000) from Cell Signaling Technology (Danvers, Mass., USA). After washes with PBS, the sections were incubated for 1.5 hrs with secondary biotinylated goat anti-rabbit antibodies, washed with PBS, and reacted in the dark for 1 hr with ABC reagents (standard Vectastain ABC Elite Kit; Vector Laboratories, Burlingame, Calif.). Then, the sections were developed with a filtered mixture of Vector SG substrate (grey) (Vector Laboratories). Immunolabeled cleaved caspase-3 neurons were quantified on photomicrographs of the superficial layers (2-4) of motor cortex (M2/1) as guided by the atlas for adult rat brain (Paxinos and Watson, 2007). The photomicrographs were taken through a 10x objective using a Hammatsu digital camera (C4742-95). The quantification was carried out as previously described (Wang et al., *Neuropsychopharmacology* 32(5): 1178-1194, 2007) by using a computer-based image analysis program, SimplePCI. The program converted all AOI (area of interest) thus defined automatically from pixels to $\mu m^2$ based on calibration files. The number of positive cells was estimated by using a double threshold technique based on boundary metrics for average neuronal size and grey level, in which two operators agreed that a gray range setting, along with the size discriminator, accurately counted the number of positive neurons. The grey level ranges were set up as 0-100 for cleaved caspase-3-positive neurons and the neuronal area sizes were be set up to range between 28 $\mu m^2$ (~6 $\mu m$ diameter) and 250 (~18 $\mu m$ diameter) $\mu m^2$. The average value from all 3-4 sections was used to represent the sub-regional value for the animal. Baseline value of immunoreactive neurons (saline treated) was subtracted from all treatments. The value of each dose treatment was normalized to that of PCP along. $IC_{50}$ and slope were analyzed and determined with the SigmaPlot four-parameter equation as described in our previous publication (Petukhov et al., *J Med Chem* 47(12): 3009-3018, 2004).

D. Image Analysis of the Density of Parvalbumin (PV)-Containing Interneurons

Early postnatal PCP administration (on PND7) has been showed to selectively reduce PV-containing interneurons in the superficial layers 2-4 of cerebral cortices including M2/1 cortex in young adulthood (PND56) (Wang et al., *Neuropsychopharmacology* 33(10): 2442-2455, 2008). Compounds showing significant AMPAR PAM effects on glutamate-induced calcium influx in HEK293 expressing hGluA1i/3i and significant preventive effect on PCP-induced caspase-3 activation in organotypic slices as well as PND7 rat pups in vivo were further defined their abilities to block PCP-induced reduction of cortical GABAergic PV-containing interneurons in young adulthood after early postnatal PCP administration.

Each candidate was tested in six (n=6) individual experiments by using PND7 rat pups from 6 different liters and following the same treatment paradigms as that in the previous section (Image analysis of cleaved Caspase-3 immunoreactive neurons). In each experiment, eight PND7 rat pups of either gender from the same liter were treated with either saline (10 ml/kg, s.c.), or PCP (10 mg/kg, s.c.), or six serial doses of a selected candidate at approximate half-log intervals log intervals (i.p., 30 min prior to PCP) followed with PCP. Pups were then be sent back to their mothers immediately after any injection, weaned on PND22, separated into groups of 4 pups/per single-sex cage and housed until the end of the experiment (on PND56). From the young adult rats, brain samples were harvested and processed as described previously (Wang et al., *Neuropsychopharmacology* 33(10): 2442-2455, 2008). For PV immunohistochemistry, neurons containing calcium binding protein PV were immunolabeled by using the ABC peroxidase system according to our protocol (Wang et al., *Neuropsychopharmacology* 33(10): 2442-2455, 2008) modified from previous publication (Solbach and Celio, *Anat Embryol (Berl)*. 184(2):103-24, 1991). Briefly, free-floating sections removed from antifreeze solution were washed with TBS (0.1 M, pH 7.4), pretreated with Triton X-100 (0.4% in TBS for 6 hrs at 4° C.), quenched for 10 min in 3% hydrogen peroxide/methanol, blocked for 1 hr with 2% BSA/10% normal goat serum/0.2% milk/0.1 M TBS and incubated for 72 hrs at 4° C. with mouse monoclonal IgG1 against PV (clone PARV-19) (1:1000, #P-3088, Sigma Chemicals, St Louis, Mo., USA). After washes with TBS, the sections were incubated for 1.5 hr with biotinylated goat anti-mouse antibodies (Vector Laboratories, Burlingame, Calif.), reacted in the dark for 1 hr with ABC reagents (standard Vectastain ABC Elite Kit; Vector Laboratories), and developed with a filtered mixture of Vector SG substrate (grey) (Vector Laboratories). PV-positive neurons were quantified on photomicrographs of the superficial layers (2-4) of motor cortex (M2/1) by using SimplePCI (Wang et al., *Neuropsychopharmacology* 33(10): 2442-2455, 2008). The number of positive cells was estimated by using a double threshold technique based on boundary metrics for average neuronal size and grey level, in which two operators agreed that a gray range setting, along with the size discriminator, accurately counted the number of positive neurons. The grey level ranges were set up as 0-100 for PV-positive neurons and the neuronal area sizes were set up to range between 28 $\mu m^2$ (~6 $\mu m$ diameter) and 250 (~18 $\mu m$ diameter) $\mu m^2$. The value of saline treated animal was used as positive control. The value of each dose treatment was normalized to that of PCP along. $EC_{50}$ and slope was analyzed and determined with the SigmaPlot four-parameter equation as described in our previous publication (Petukhov et al., *J Med Chem* 47(12): 3009-3018, 2004).

E. Assessment of Locomotor Activity

Rodents treated with NMDAR open channel blockers such as PCP during the early postnatal period developed behavior deficits (including increased locomotor activity) in adulthood which resemble behavioral abnormalities typically present in schizophrenia (Fredriksson and Archer, *Neurotox Res* 6(6): 435-456, 2004; Harris et al., *Eur J Neurosci* 18(6): 1706-1710, 2003; Anastasio and Johnson, *Pharmacol Biochem Behav* 90: 569-577, 2008). Compounds showing significant AMPAR PAM effects on glutamate-induced calcium influx in HEK293 expressing hGluA1i/3i, and significant preventive effect on PCP-induced caspase-3 activation in organotypic slices and PND7 rat pups in vivo and on PCP-induced long lasting deficit of cortical GABAergic PV-containing interneurons were tested the ability to correct behavior deficits in young adulthood after early postnatal PCP administration.

Two sets of experiments were executed. The first set was conducted to test if early postnatal pretreatment of a compound of invention prior to PCP injection prevented PCP-induce abnormal locomotor activity in young adulthood. Each candidate was tested in ten (n=10) individual experiments by using PND7 rat pups from 10 different liters. In each experiment, five PND7 rat pups of either gender from the same liter were treated with either saline (10 ml/kg, s.c.), or PCP (10 mg/kg, s.c.), or three serial doses of a selected candidate at log intervals (i.p., 30 min prior to PCP) followed by PCP (10 mg/kg) injection. Pups were then be sent back to their mothers immediately after any injection, weaned on PND22, separated into groups of 4 pups/per single-sex cage and housed until the end of the experiment. On PND56, all animals were tested with PCP (4 mg/kg, sc)-challenged locomotor activity as described previously (Phillips et al, *J Pharmacol Exp Ther.* 296 (3): 905-13, 2001).

The second set of experiments was performed to see whether late treatment of a compound of invention after PCP injection correct early postnatal PCP injection-induced adulthood behavior deficit. Each candidate was tested in ten (n=10) individual experiments by using PND7 rat pups from 10 different liters. In each experiment, five PND7 rat pups of either gender from the same liter were treated with either saline (10 ml/kg, s.c.), or PCP (10 mg/kg, s.c.). Pups were then sent back to their mothers immediately after any injection, weaned on PND22, separated into groups of 4 pups/per single-sex cage and housed until the end of the experiment. ON PND50, the animals were injected with saline or one of the three serial doses (doses that most effectively block PCP-induced acute neuroapoptosis on PND7 and long lasting deficit of cortical GABAergic PV neurons in young adulthood) of a selected candidate at log intervals, once a day for 5 consecutive days. On PND56, all animals were tested with PCP (4 mg/kg, sc)-challenged locomotor activity as previously described (Phillips et al, *J Pharmacol Exp Ther.* 296 (3): 905-13, 2001).

For locomotor activity assessment, animals were placed in locomotor chamber boxes and allowed to habituate for 30 min prior to a 4 mg/kg challenge dose of PCP (i.p.). Locomotor activity was measured for an additional 90 min via an open-field activity system (San Diego Instruments, San Diego, Calif.) comprised of four individual Plexiglas enclosures (40×40×40 cm) consisting of a 4×4 photobeam matrix to measure central and peripheral activity. The number of horizontal (central+peripheral activity) photobeam interruptions were recorded in 5-min bins. Data were analyzed as horizontal (peripheral plus central) activity counts totaled for the 90-min test session following s.c. injection of PCP or its saline control. Because group comparisons were specifically defined before the start of the experiment, these planned comparisons were conducted in lieu of an overall F test in a multifactorial ANOVA; this statistical analysis has been supported in a number of statistical texts (e.g., Keppel, 1973). Thus, each experiment was subjected to a one-way ANOVA with levels of the treatment factor corresponding to the three to four drug combinations administered in that experiment. Planned, pairwise comparisons of the treatment means were made with the help of SigmaStat statistical software (Jandel, San Rafael, Calif.). All statistical analyses were conducted with an experiment-wise error rate of α=0.05 (Phillips et al, *J Pharmacol Exp Ther.* 296 (3): 905-13, 2001).

F. Tail-Flick Test.

Figure 9A:
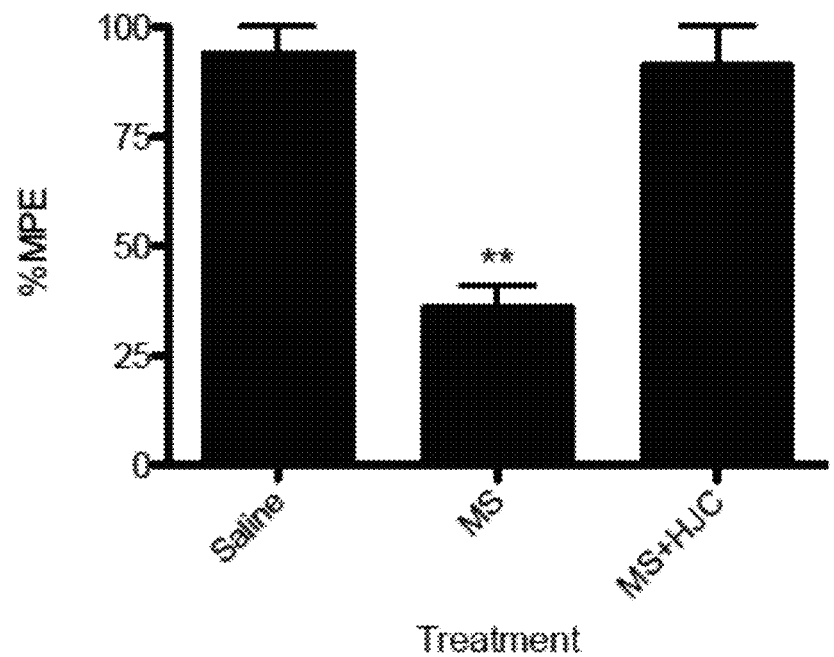
FIGS. 9A-9B HJC-1-22 10 mg/kg reversed established morphine tolerance (A) and partially reversed physical dependence (B).
Figures 10A, 10B:
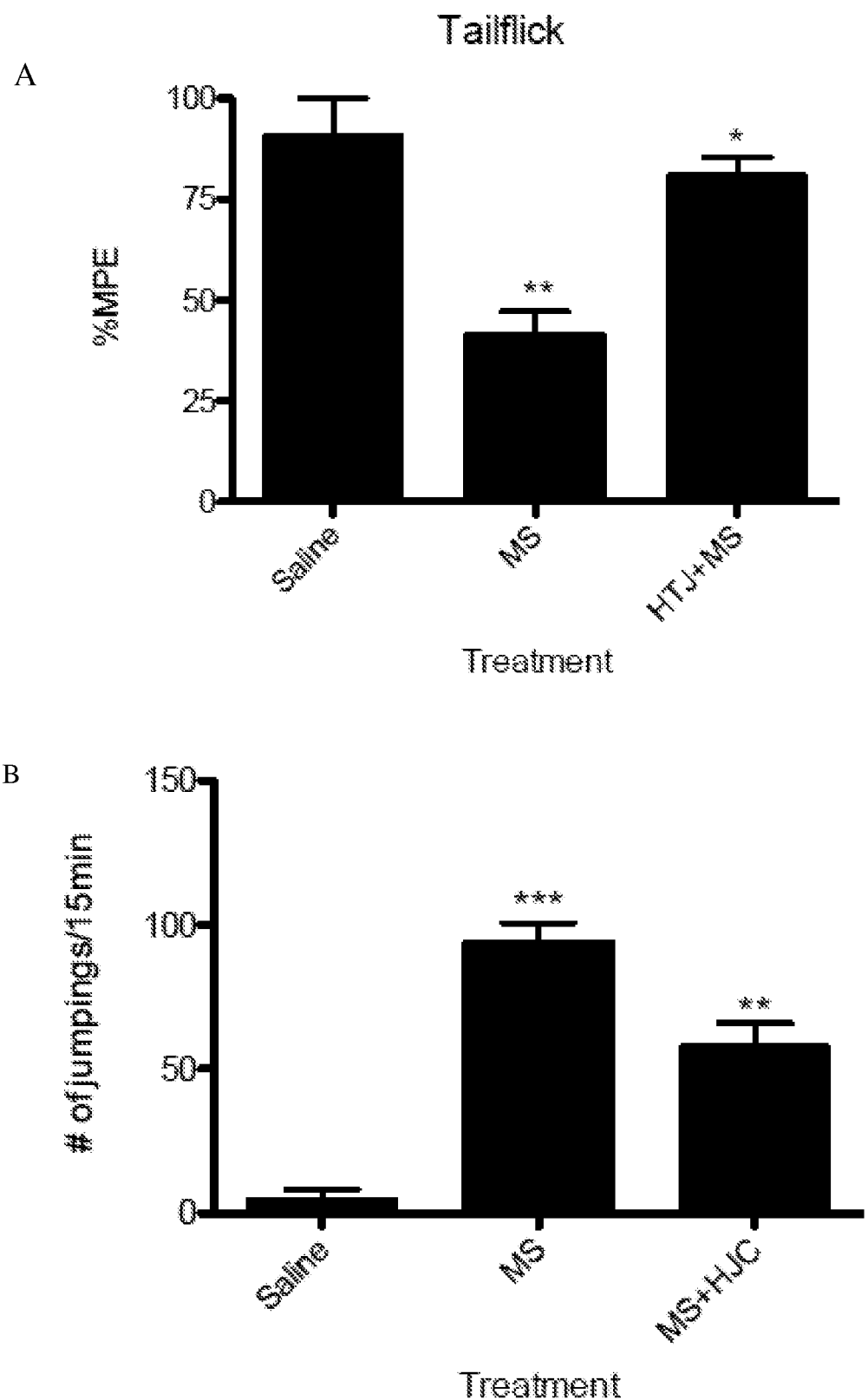
FIG. 10A-10B HJC-1-22 10 mg/kg prevented the development of morphine tolerance (A) and partially prevented physical dependence (B).

The tail-flick test was used to determine basal nociception and morphine antinociception as described previously (Wang et al., *J Neurosci* 21:1779-86, 2001; Tang et al., *J Pharmacol Exp Ther* 317:901-909, 2006). In brief, One third of the distal portion of mouse tail was immersed into a water bath maintained at 52° C., and the latency of a quick tail-flick response was recorded. Morphine-antinociception was evaluated 30 min after a test dose of morphine (10 mg/kg s.c. unless otherwise stated) and is expressed as the percentage of maximal possible effect (MPE). MPE %=100%×(postdrug latency–predrug latency)/(cutoff–predrug latency). A 12-s cutoff time was used to prevent tissue damage (FIG. 9A and FIG. 10A).

G. Chronic Opioid Tolerance and Dependence.

Figure 9B:
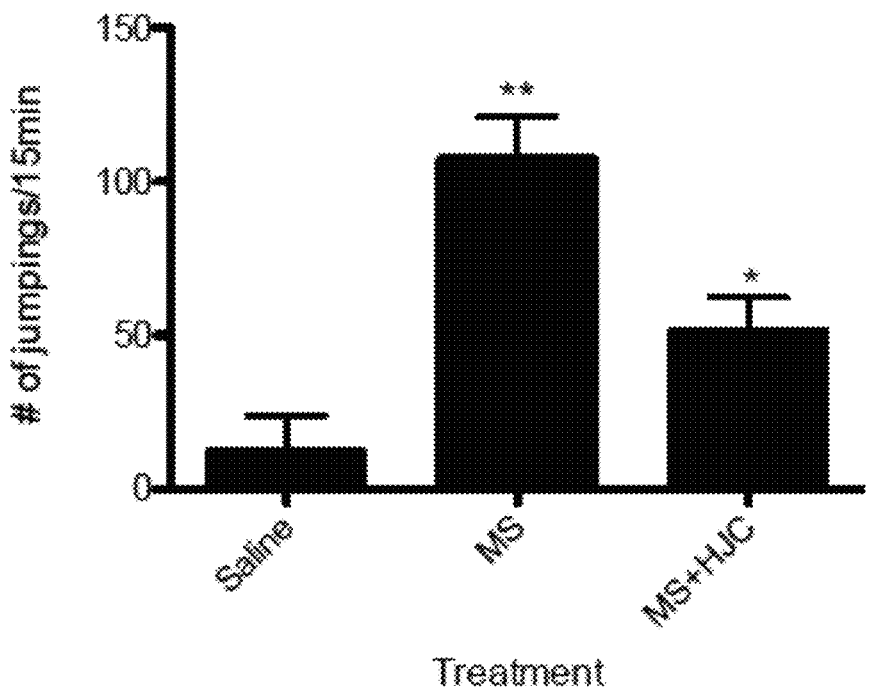

To induce chronic opioid tolerance and dependence, mice were treated with morphine (10 mg/kg s.c., given at 8:00 AM and 6:00 PM) for 5 days (Herz and Teschemacher, *Experientia* 29:64-65, 1973). Control mice received an equal number and volume of injections with saline. Morphine tolerance and naloxone-precipitated withdrawal were evaluated. Haloperidol (0.1-1.0 mg/kg i.p. or p.o.) was given 30 min before the test dose of morphine or naloxone (FIG. 9B and FIG. 10B).

The invention claimed is:

1. A positive allosteric modulator of AMPA receptors (AMPAR) having a general formula of Formula I:

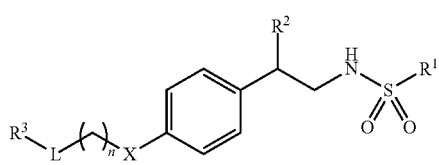

Formula I where $R^1$ and $R^2$ are independently hydrogen, $C_1$-$C_6$ alkyl or $C_1$-$C_6$ heteroalkyl; and $R^3$ is hydrogen, nitro, amine, cyano, substituted or unsubstituted sulfonyl, substituted or unsubstituted acyl, substituted or unsubstituted alkyl, substituted or unsubstituted heteroalkyl, substituted or unsubstituted cycloalkyl, substituted or unsubstituted heterocyclyl, substituted or unsubstituted aryl, or a substituted or unsubstituted heteroaryl; and n is 0; and L is —C(O)—;

X is a indole, indazole, or pyridine.

2. The positive allosteric modulator of claim 1, wherein $R^1$ and $R^2$ are independently $C_1$-$C_6$ alkyl.

3. The positive allosteric modulator of claim 1, wherein $R^1$ is methyl or isopropyl.

4. The positive allosteric modulator of claim 1, wherein $R^2$ is methyl.

5. The positive allosteric modulator of claim 1, wherein X is pyridine.

6. The positive allosteric modulator of claim 1, wherein $R^3$ is substituted or unsubstituted N-containing $C_5$-$C_6$ heterocyclyl.

7. The positive allosteric modulator of claim 1, wherein the modulator is selected from Propane-2-sulfonic acid (2-{4-[2-(pyrrolidine-1-carbonyl)-pyridin-4-yl]-phenyl}-propyl)-amide (HJC-1-22); Propane-2-sulfonic acid (2-{4-[5-(piperidine-1-carbonyl)-indol-1-yl]-phenyl}-propyl)amide (HJC-1-24); Propane-2-sulfonic acid (2-{4-[5-(piperidine-1-carbonyl)-pyridin-2-yl]-phenyl}-propyl)-amide (HJC-1-59); Propane-2-sulfonic acid (2-{4-[5-(piperidine-1-carbonyl)-indazol-1-yl]-phenyl}-propyl)-amide (HJC-2-8); Propane-2-sulfonic acid (2-{4-[5-(pyrrolidine-1-carbonyl)-indol-1-yl]-phenyl}-propyl)amide (HJC-2-10); Propane-2-sulfonic acid (2-{4-[5-(4-methyl-piperazine-1-carbonyl)-indol-1-yl]-phenyl}-propyl)amide (HJC-2-22); Propane-2-sulfonic acid (2-{4-[5-(piperazine-1-carbonyl)-indol-1-yl]-phenyl}-propyl)amide (HJC-2-37); Propane-2-sulfonic acid (2-{4-[5-(4-methanesulfonyl-piperazine-1-carbonyl)-indol-1-yl]-phenyl}-propyl)amide (HJC-2-67); Propane-2-sulfonic acid (2-{4-[5-(4-acetyl-piperazine-1-carbonyl)-indol-1-yl]-phenyl}-propyl)amide (HJC-2-68); Propane-2-sulfonic acid (2-{4-[2-(piperidine-1-carbonyl)-pyridin-4-yl]-phenyl}-propyl)-amide (HJC-2-69); or Propane-2-sulfonic acid (2-{4-[5-(pyrrolidine-1-carbonyl)-pyridin-2-yl]-phenyl}-propyl)-amide (HJC-2-70).

8. The positive allosteric modulator of claim 1, wherein the modulator is Propane-2-sulfonic acid (2-{4-[2-(pyrrolidine-1-carbonyl)-pyridin-4-yl]-phenyl}-propyl)-amide (HJC-1-22).

* * * * *